US009453210B2

(12) United States Patent
Becker et al.

(10) Patent No.: US 9,453,210 B2
(45) Date of Patent: Sep. 27, 2016

(54) CELLS AND METHOD FOR PRODUCING ACETONE

(75) Inventors: Franz Ulrich Becker, Freigericht-Horbach (DE); Gerda Grund, Coesfeld (DE); Matthias Orschel, Muenster (DE); Kai Doderer, Rodgau (DE); Gerd Loehden, Essen (DE); Gerd Brand, Nottuln/Schapdetten (DE); Peter Duerre, Ulm (DE); Simone Thum, Ulm (DE); Hubert Johannes Bahl, Rostock (DE); Ralf-Joerg Fischer, Kritzmow (DE); Antje May, Rostock (DE)

(73) Assignee: Evonik Degussa GmbH, Essen (DE)

( * ) Notice: Subject to any disclaimer, the term of this patent is extended or adjusted under 35 U.S.C. 154(b) by 269 days.

(21) Appl. No.: 13/260,012

(22) PCT Filed: Feb. 23, 2010

(86) PCT No.: PCT/EP2010/052244
§ 371 (c)(1),
(2), (4) Date: Sep. 23, 2011

(87) PCT Pub. No.: WO2010/121849
PCT Pub. Date: Oct. 28, 2010

(65) Prior Publication Data
US 2012/0101304 A1 Apr. 26, 2012

(30) Foreign Application Priority Data
Apr. 23, 2009 (DE) .................. 10 2009 002 583

(51) Int. Cl.
| C12N 1/20 | (2006.01) |
|---|---|
| C12P 7/30 | (2006.01) |
| C07H 21/04 | (2006.01) |
| C07C 49/04 | (2006.01) |
| C07C 49/20 | (2006.01) |
| C12N 9/10 | (2006.01) |
| C12N 9/16 | (2006.01) |
| C12N 9/88 | (2006.01) |

(52) U.S. Cl.
CPC .............. *C12N 9/13* (2013.01); *C12N 9/1029* (2013.01); *C12N 9/16* (2013.01); *C12N 9/88* (2013.01); *C12P 7/30* (2013.01); *C12Y 203/01009* (2013.01); *Y02P 20/52* (2015.11)

(58) Field of Classification Search
None
See application file for complete search history.

(56) References Cited

U.S. PATENT DOCUMENTS

| 2010/0261237 A1 | 10/2010 | Verseck et al. |
| 2013/0261343 A1 | 10/2013 | Orschel et al. |

FOREIGN PATENT DOCUMENTS

WO 2009 056423 5/2009

OTHER PUBLICATIONS

Bermejo et al. Expression of Clostridium acetobutylicum ATCC 824 Genes in *Escherichia coli* for Acetone Production and Acetate Detoxification, Applied and Environmental Microbiology, Mar. 1998, p. 1079-1085.*
Lacy Daniels, Comments on Enzymatic Synthesis of Organic Acids and Alcohols from H2, CO2, and CO, Biotechnology and Bioengineering, vol. XXIV, pp. 2099-2102 (1982).*
Jones et al. Microbiol. Rev. (1986), 50(4): 484-524.*
Mermelstein, L. D. et al., "Metabolic Engineering Of Clostridium Acetobutylicum ATCC 824 For Increased Solvent Production By Enhancement Of Acetone Formation Enzyme Activities Using A Synthetic Acetone Operon", Biotechnology and Bioengineering, vol. 42, No. 9, pp. 1053-1060, XP-002579042, (1993).
Mollah, A. H. et al., "The Influence Of $H_2$, $CO_2$ And Dilution Rate On The Continuous Fermentation Of Acetone-Butanol", Applied Microbiology and Biotechnology, vol. 37, No. 5, pp. 533-538, XP-009132534, (Jan. 1, 1992).
Kim, B. H. et al., "Control Of Carbon And Electron Flow In Clostridium Acetobutylicum Fermentations: Utilization Of Carbon Monoxide To Inhibit Hydrogen Production And To Enhance Butanol Yields", Applied and Environmental Microbiology, vol. 48, No. 4, pp. 764-770, XP-002579043, (1984).
International Search Report Issued May 7, 2010 in PCT/EP10/052244 filed Feb. 23, 2010.
U.S. Appl. No. 14/116,233, filed Nov. 7, 2013, Orschel, et al.
U.S. Appl. No. 14/124,486, filed Dec. 6, 2013, Nitz, et al.
European Office Action issued Jan. 5, 2015 in Patent Application No. 10 704 577.5.
Anne M. Henstra, et al., "Microbiology of synthesis gas fermentation for biofuel production" Current Opinion in Biotechnology, vol. 18, No. 3, XP022110181, Jun. 8, 2007, pp. 200-206.
Office Action in Australian Patent Application No. 2010241185, dated Jul. 6, 2015.
Decision of Refusal in corresponding Japanese Patent Application No. 2012-506411, dated Mar. 23, 2015. (w/English Translation).
J. Wong, et al., "Recombination-Induced Variants of Clostridium acetobutylicum ATCC 824 with Increased Solvent Production", Current Microbiology, vol. 32, 1996, pp. 349-356.

* cited by examiner

*Primary Examiner* — Iqbal H Chowdhury
(74) *Attorney, Agent, or Firm* — Oblon, McClelland, Maier & Neustadt, L.L.P.

(57) ABSTRACT

The invention relates to cells and a method for producing acetone.

21 Claims, 4 Drawing Sheets

CELLS AND METHOD FOR PRODUCING ACETONE

CROSS-REFERENCE TO RELATED APPLICATIONS

The present application is a 35 U.S.C. §371 national stage patent application of International patent application PCT/EP2010/052244, filed on Feb. 23, 2010, published as WO/2010/121849 on Oct. 28, 2010, the text of which is incorporated by reference, and claims the benefit of the filing date of German application no. 102009002583.9, filed on Apr. 23, 2009, the text of which is also incorporated by reference.

FIELD OF THE INVENTION

The invention relates to cells and a method for producing acetone.

PRIOR ART

ABE Process in *Clostridium*

The classical ABE fermentation process, i.e. the microbial production of acetone, butanol and ethanol, was for a long time the world's second-largest biotechnological process, directly after the fermentation of ethanol with yeasts. Commercial ABE fermentation began in 1916 in England, where inter alia Chaim Weizmann discovered that *Clostridium acetobutylicum* is able to form the solvents acetone, butanol and ethanol. The process was employed in the West until the late 1950s, and in South Africa even until 1981.

There are two main reasons why this process was abandoned: on the one hand, the chemical synthesis of acetone and butanol became more and more favorable, and on the other hand the price for the substrates for fermentation rose sharply. There was in particular a large increase in the price for molasses, on account of its use as a feed additive for cattle.

The increasing costs for petrochemical starting products, and new technological possibilities in the area of pathway engineering of microorganisms, now open up new options for the development of high-performance strains and commercial fermentation processes for the production of solvents such as acetone.

The classical ABE fermentation is based on the organisms *Clostridium acetobutylicum* and *Clostridium beijerinckii*. Both are Gram-positive and multiply under strictly anaerobic conditions. These organisms can convert mono-, di- and polysaccharides, and the substrates mainly used in fermentation are molasses and starch.

The fermentation process with *C. acetobutylicum* is divided into two phases. In the first phase, biomass formation is accompanied by the formation of acetate, butyrate and traces of ethanol ("acidogenic phase"). In the second phase, the so-called "solventogenic phase", the acids are then used for forming the fermentation products acetone, butanol and ethanol (ABE). The products acetone, butanol and ethanol are formed in wild-type *C. acetobutylicum* in the approximate proportions 3:6:1. These proportions of the products can vary widely, depending on the chosen culture conditions (e.g. pH or nutrient feed) or the substrates used.

Figure 1:
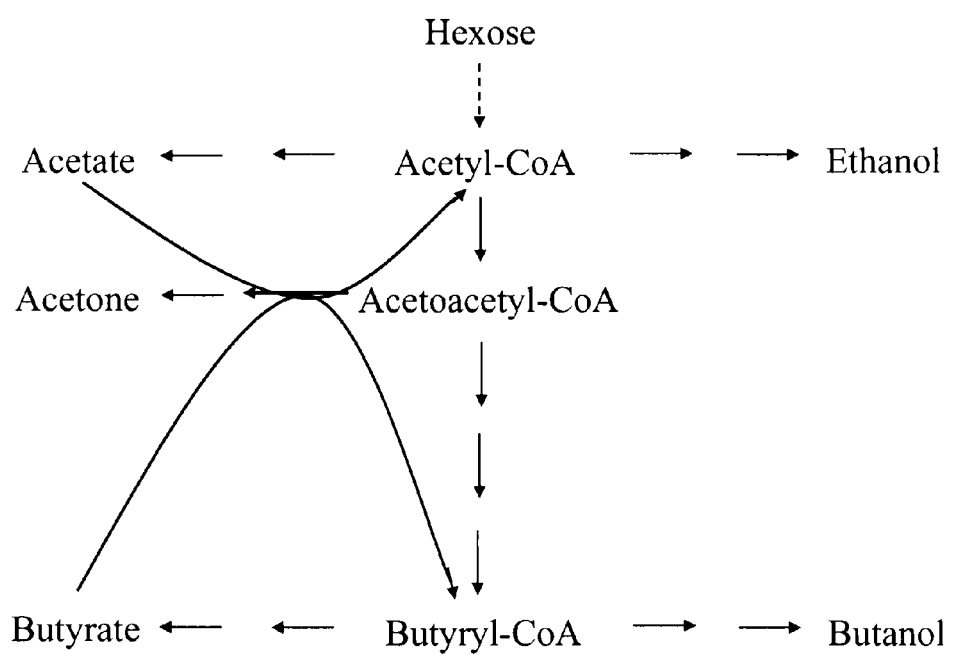

The enzymes of solvent biosynthesis of acetone, butanol and ethanol have been extensively purified and characterized biochemically (cf. FIG. 1; Duerre, P., and Bahl, H. 1996. Microbial production of acetone/butanol/isopropanol. In: Biotechnology, Vol. 6, 2nd ed. M. Roehr, (ed.), VCH Verlagsgesellschaft mbH, Weinheim, Germany. p. 229-268. Duerre, P. 1998. New insights and novel developments in clostridial acetone/butanol/isopropanol fermentation. Appl. Microbiol. Biotechnol. 49: 639-648). The genome sequence of *C. acetobutylicum* is also available (Noelling, J., Breton, G., Omelchenko, M. V. & 16 other authors (2001). Genome sequence and comparative analysis of the solvent-producing bacterium *Clostridium acetobutylicum*. J Bacteriol 183, 4823-4838).

*Clostridium acetobutylicum* strains have already been generated in which the production of acetone has been decoupled from the production of butanol and ethanol, so that these strains only produce acetone (Mermelstein et al. (1993). Metabolic engineering of *Clostridium acetobutylicum* ATCC824 for increased solvent production by enhancement of acetone formation enzyme activities using a synthetic operon. Biotech. Bioeng. 42:1053-1060; Nair, R. V., and Papoutsakis, E. T. 1994). The measured titers for acetone were always below its concentrations in the wild type.

Figure 2:
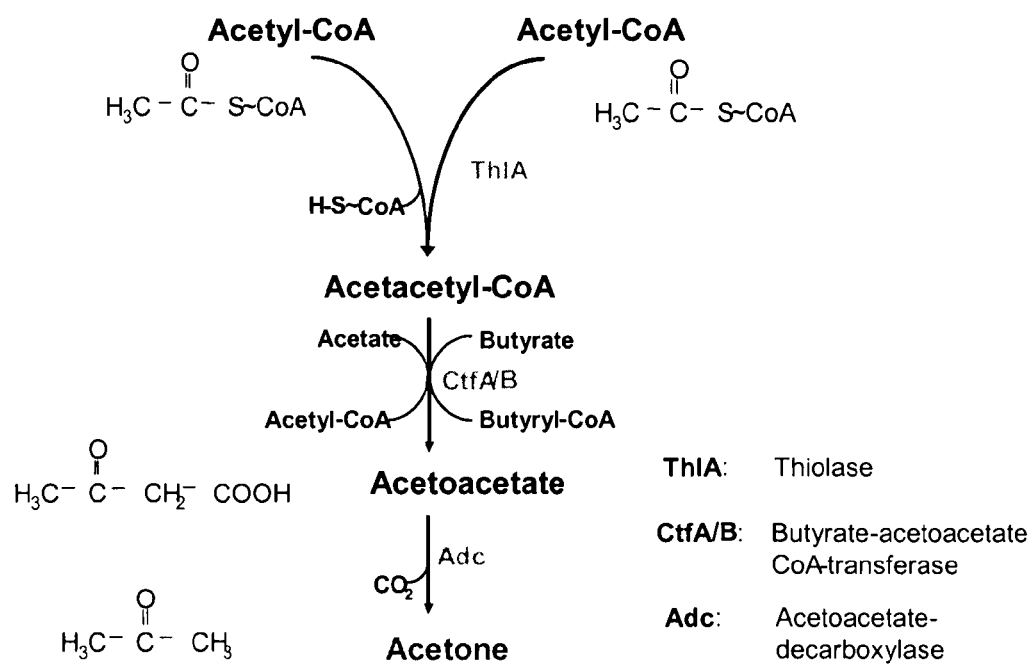

FIG. 2 shows the classical metabolic pathway for acetone synthesis, characterized in *Clostridium*. This pathway starts with acetyl-CoA, a central metabolite that is formed in all microorganisms, regardless of the carbon source that is metabolized or which metabolic pathways are established. The required enzymes are: β-ketothiolase, the two subunits of acetyl-CoA/butyryl-CoA-transferase, and acetoacetate decarboxylase.

It has been shown that the heterologous expression of these enzymes from *C. acetobutylicum* in *Escherichia coli*, which catalyze acetone formation starting from acetyl-CoA (acetoacetate decarboxylase, acetyl-CoA/butyryl-CoA-transferase and thiolase) lead to acetone formation in this organism of approx. 150 mM, but there was the disadvantage that large amounts of acetate (50 mM) were also produced (Bermejo L. L., N. E. Welker, E. T. Papoutsakis. 1998. Expression of *Clostridium acetobutylicum* ATCC 824 Genes in *Escherichia coli* for Acetone Production and Acetate Detoxification. Appl. Env. Microbiol. 64:1079-1085).

Another disadvantage here is that acetone was only produced under aerobic conditions, as the redox equivalents that are formed during the metabolization of glucose to acetyl-CoA cannot be re-oxidized by *E. coli* under anaerobic conditions.

A disadvantage common to all the processes described is that they require complex carbon sources, for example sugars.

Acetogenic Cells

Acetogenic cells, i.e. cells that are able to form acetate by means of anaerobic respiration, are known.

The acetogenic bacteria include e.g. species of the genus *Acetobacterium* such as *A. woodii* and *Clostridium aceticum*.

WO0068407 describes the use of acetogenic bacteria for the production of ethanol.

The genome sequence of *C. ljungdahlii* has also recently been made available. A genome sequence has not yet been published for *C. aceticum* and *C. carboxidivorans*. It is known, however, that *C. aceticum* additionally carries a plasmid (5.6 kbp, Lee et al., 1987). At present, no techniques have been published for genetically modifying these organisms.

The group of the acetogenic bacteria belongs to the anaerobic prokaryotes that are able to utilize $CO_2$ as terminal electron acceptor, forming acetate. At present, 21 different genera have been assigned to the acetogens (Drake et al., 2006), including some Clostridia (Drake & Küsel, 2005). They are able to use carbon dioxide plus hydrogen or even carbon monoxide as the carbon and energy source (Wood, 1991). In addition, alcohols, aldehydes, carboxylic acids and numerous hexoses can also be used as the carbon source (Drake et al., 2004). The reductive metabolic pathway that leads to the formation of acetate is called the acetyl-CoA or Wood-Ljungdahl pathway.

The problem to be solved by the invention was to provide a method by which acetone can be produced from ubiquitously available carbon sources.

DESCRIPTION OF THE INVENTION

It was found, surprisingly, that the cells and the method described hereunder solve the problem of the invention.

The present invention therefore relates to cells as described in claim 1.

The invention also relates to a method for producing acetone with the cells according to the invention.

One advantage of the invention is that the cells can be anaerobic and therefore can be cultivated particularly favorably in energy terms.

Another advantage of the invention is that the cells according to the invention contribute to a decrease of the climate-damaging carbon dioxide.

Yet another advantage of the cells according to the invention is an increased yield through acetone production from carbon dioxide and hydrogen.

The present invention relates to an acetogenic cell, which is able to form acetone.

The term "acetogenic cell" in the context of the present invention means cells that are able to form acetate by means of anaerobic respiration.

All percentages given are, unless stated otherwise, percentages by weight.

Preferably the acetogenic cell is an isolated, in particular a genetically modified cell.

According to the invention, a cell is preferred which, selected from at least one carbon source from the group comprising carbon dioxide and carbon monoxide, is able to form acetone. Especially preferably the acetogenic cell according to the invention is able to form acetone from carbon monoxide and carbon dioxide as the sole carbon source.

It is well known by a person skilled in the art that product yields in biological systems can be improved by means of recombinant gene technology. Therefore it is further preferred according to the invention for the acetogenic cell to be genetically modified relative to its wild type, so that it is able to form more acetone compared with its wild type.

The formulation "so that it is able to form more acetone compared with its wild type" also relates to the case when the wild type of the genetically modified cell is unable to form any acetone at all, or at least no detectable amounts of this compound, and it is only after the genetic modification that detectable amounts of this component can be formed.

A "wild type" of a cell preferably means a cell whose genome is in a state such as arose naturally by evolution. The term is used both for the whole cell and for individual genes. The term "wild type" therefore in particular does not include such cells or such genes whose gene sequences have been altered at least partially by human intervention by means of recombinant techniques.

These cells are preferably genetically modified so that they can form more acetone from a carbon source, compared with their wild type.

Moreover, it is preferable according to the invention that the acetogenic cell has been genetically modified so that in a defined time interval, preferably within 2 hours, more preferably within 8 hours and most preferably within 24 hours, it forms at least 2 times, especially preferably at least 10 times, more preferably at least 100 times, even more preferably at least 1000 times and most preferably at least 10 000 times more acetone than the wild-type cell. The increase in product formation can be determined for example by cultivating the cell according to the invention and the wild-type cell each separately under identical conditions (same cell density, same nutrient medium, same culture conditions) in a suitable nutrient medium for a specified time interval and then determining the amount of target product (acetone) in the nutrient medium.

In this connection it is preferable for the cell to have increased activity, compared with its wild type, of at least one of the following enzymes:

an enzyme $E_1$, which catalyzes the reaction of acetyl-coenzyme A to acetoacetyl-coenzyme A;

an enzyme $E_2$, which catalyzes the reaction of acetoacetyl-coenzyme A to acetoacetate;

an enzyme $E_3$, which catalyzes the reaction of acetoacetate to acetone.

The formulation "an increased activity of an enzyme $E_x$" used in the foregoing and hereinafter preferably always means an activity of the respective enzyme $E_x$ increased by a factor of at least 2, especially preferably of at least 10, more preferably of at least 100, even more preferably of at least 1000 and most preferably of at least 10 000. Furthermore, the cell according to the invention, which has "an increased activity of an enzyme $E_x$ compared with its wild type", in particular also comprises a cell whose wild type has no or at least no detectable activity of this enzyme $E_x$ and only displays a detectable activity of this enzyme $E_x$ after increasing the enzyme activity, for example by overexpression. In this connection, the term "overexpression" or the formulation "increase in expression" used hereinafter also comprises the case when a starting cell, for example a wild-type cell, has no or at least no detectable expression and it is only by recombinant techniques that a detectable expression of the enzyme $E_x$ is induced.

In this connection, especially preferred cells are those in which the activity of the following enzyme or enzymes is increased: $E_1$, $E_2$, $E_3$, $E_1+E_2$, $E_1+E_3$, $E_2+E_3$, $E_1+E_2+E_3$, with $E_1+E_2+E_3$ being especially preferred.

Furthermore, it is preferable according to the invention for the enzyme $E_1$ to be an acetyl-CoA-C-acetyl transferase (EC 2.3.1.9); for the enzyme $E_2$ to be a butyrate-acetoacetate-CoA-transferase (EC 2.8.3.9) or an acyl-CoA-hydrolase (EC 3.1.2.20); for the enzyme $E_3$ to be an acetoacetate decarboxylase (EC 4.1.1.4).

Especially preferably, the enzyme used as enzyme $E_1$ is thlA from *Clostridium acetobutylicum*.

Especially preferably, butyrate-acetoacetate-CoA-transferase used as enzyme $E_2$ comprises ctfA and ctfB from *Clostridium acetobutylicum* and atoD and atoA from *Escherichia coli*.

Especially preferably, acyl-CoA hydrolase used as enzyme $E_2$ comprises tell from *B. subtilis* or ybgC from *Haemophilus influenzae*.

Especially preferably, the enzyme used as enzyme $E_3$ is adc from *Clostridium acetobutylicum*.

The acetogenic cell according to the invention is preferably a microorganism, preferably a bacterium and especially preferably an anaerobic bacterium, in particular a rod-shaped, Gram-positive bacterium.

Quite especially preferably, acetogenic cells are used that are selected from the group comprising *Thermoanaerobacter kivui, Acetobacterium woodii, Acetoanaerobium notera, Clostridium aceticum, Butyribacterium methylotrophicum, Clostridium acetobutylicum, Moorella thermoacetica, Eubacterium limosum, Peptostreptococcus productus, Clostridium ljungdahlii* and *Clostridium carboxidivorans*. An especially suitable bacterium is *Clostridium carboxidivorans*, in particular strains such as "P7" and "P11". Said cells are described for example in US 2007/0275447 and US 2008/0057554.

Another especially suitable bacterium is *Clostridium ljungdahlii*, in particular strains selected from the group comprising *Clostridium ljungdahlii* PETC, *Clostridium ljungdahlii* ER12, *Clostridium ljungdahlii* C01 and *Clostridium ljungdahlii* O-52 and are described in WO 98/00558 and WO 00/68407.

The invention also relates to a method for producing acetone, comprising the process steps: A) contacting a cell according to the invention with a nutrient medium comprising at least one carbon source selected from the group comprising carbon dioxide and carbon monoxide, B) cultivating the cell under conditions that enable the cell to form acetone and C) optionally isolating the acetone that formed.

The acetogenic cell according to the invention is able, preferably under anaerobic conditions, to form acetone from at least one carbon source selected from the group comprising carbon dioxide and carbon monoxide.

Regarding the source of these substrates, it is evident that there are many possible sources for providing CO or $CO_2$ as the carbon source. It can be seen that in practice, the carbon source used in the present invention can be any gas or gas mixture that is able to supply the acetogenic cell with sufficient amounts of carbon, so that it is able to perform its anaerobic respiration and form acetone.

In the method according to the invention it is preferable for the carbon source to be provided by waste gases, for example synthesis gas, flue gas, oil refinery waste gases, gases produced by yeast fermentation or clostridial fermentation, waste gases from the gasification of cellulose-containing materials or coal gasification.

These waste gases need not necessarily have been formed as side effects of other processes, but can be produced specially for use in the method according to the invention.

It can be seen that in practice the carbon source used for the present invention can be any waste gas that is able to supply the acetogenic cell with sufficient amounts of carbon, so that it can perform its anaerobic respiration.

In a preferred embodiment of the method according to the invention, the carbon source is synthesis gas.

Synthesis gas can for example be prepared from the by-product of coal gasification. The acetogenic cell therefore converts a substance that is a waste product into a valuable raw material. Alternatively synthesis gas can be provided for the method according to the invention by gasification of widely available, low-cost agricultural raw materials.

There are numerous examples of raw materials that can be converted to synthesis gas, as almost all forms of vegetation can be used for this purpose. Preferred raw materials are selected from the group comprising perennial grasses such as zebra grass, cereal residues, processing wastes such as sawdust.

Generally synthesis gas is obtained in a gasifier from dried biomass, mainly by pyrolysis, partial oxidation and steam reforming, wherein the primary products are CO, $H_2$ and $CO_2$. Normally a proportion of the product gas is reprocessed, in order to optimize product yields and avoid tar formation.

Cracking of the unwanted tar into synthesis gas and CO can be carried out using lime and/or dolomite. These processes are described in detail in e.g. Reed, 1981 (Reed, T. B., 1981, Biomass gasification: principles and technology, Noyes Data Corporation, Park Ridge, N.J.).

Mixtures of various sources can also be used as the carbon source.

The nutrient media used in the method according to the invention must suitably satisfy the requirements of the particular strains. Descriptions of nutrient media for various microorganisms are given in the manual "Manual of Methods for General Bacteriology" of the American Society for Bacteriology (Washington D.C., USA, 1981).

Besides the carbon sources, the nutrient medium contains in particular nitrogen and phosphorus sources, salts and pH control agents.

The nitrogen source used can be organic nitrogen-containing compounds such as peptones, yeast extract, meat extract, malt extract, corn-steep liquor, soybean flour and urea or inorganic compounds such as ammonium sulfate, ammonium chloride, ammonium phosphate, ammonium carbonate and ammonium nitrate. The nitrogen sources can be used individually or as a mixture.

As the phosphorus source, the nutrient medium can contain phosphoric acid, potassium dihydrogen phosphate or dipotassium hydrogen phosphate or the corresponding sodium-containing salts. The culture medium must additionally contain metal salts, e.g. magnesium sulfate or iron sulfate, which are necessary for growth. Finally, essential growth promoters such as amino acids and vitamins can be used in addition to the aforementioned substances.

The stated feed materials can be added to the culture in the form of a single preparation or can be supplied in a suitable manner during cultivation.

For controlling the pH of the culture, basic compounds such as sodium hydroxide, potassium hydroxide, ammonia or ammonia water or acidic compounds such as phosphoric acid or sulfuric acid can be used appropriately. To control the formation of foam, antifoaming agents such as fatty acid polyglycol esters can be used. To maintain the stability of plasmids, suitable substances with selective action, e.g. antibiotics, can be added to the medium.

In process step B) of the method according to the invention, the acetogenic cells are cultivated under conditions that allow the cell to form acetone. Preferably said culture takes place under anaerobic conditions.

The genetically modified cells according to the invention can be brought in contact with the nutrient medium continuously or discontinuously in a batch process or in a fed-batch process or repeated-fed-batch process, and therefore cultivated, for the purpose of producing acetone.

A semi-continuous process is also conceivable, as described in GB-A-1009370. A summary of known culture techniques is described in Chmiel's textbook ("Bioprozesstechnik 1. Einführung in die Bioverfahrenstechnik" ["Bioprocess technology 1. Introduction to bioprocess technology"] (Gustav Fischer Verlag, Stuttgart, 1991)) or in the textbook by Storhas ("Bioreaktoren and periphere Einrichtungen" ["Bioreactors and peripheral equipment"], Vieweg Verlag, Brunswick/Wiesbaden, 1994).

Other very suitable methods for cultivation of the acetogenic cell in process step b) are described e.g. in the DOE report "Bench-scale Demonstration of Biological Production of Ethanol from Coal Synthesis Gas", Topical Report 5, November 1995 (DOE Contract Number DE-AC22-92PC92118) and in documents WO 98/00558, WO 00/68407 and WO 02/08438.

In step C) of the method according to the invention, the acetone formed by the cells can optionally be isolated from the cells and/or the nutrient medium, wherein all the methods for isolating low-molecular substances from complex compositions known by a person skilled in the art may be considered for isolation.

As examples we may mention at this point precipitation by means of suitable solvents, extraction by means of suitable solvents, complexation, for example by means of cyclodextrins or cyclodextrin derivatives, crystallization, purification or isolation by chromatographic methods or transformation of the acetone into derivatives that can be separated easily.

In particular, methods of separation by distillation are suitable for use in process step C).

The acetone obtainable from the method according to the invention also forms part of the present invention.

In the examples presented below, the present invention is described by way of illustration, but the invention, the scope of which follows from the complete description and the claims, is not to be limited to the embodiments presented in the examples.

The following figures form part of the disclosure:

FIG. 1: Biosynthetic pathway of the classical, clostridial ABE process

FIG. 2: Biosynthetic pathway of acetone in *C. acetobutylicum*

Figure 3:
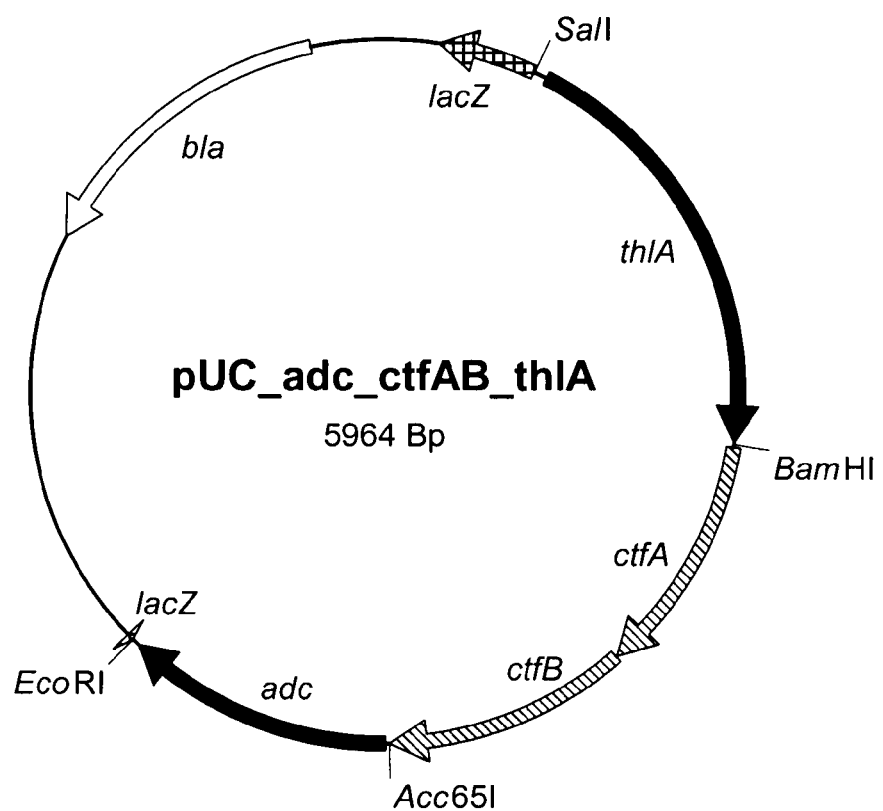
Figure 4:
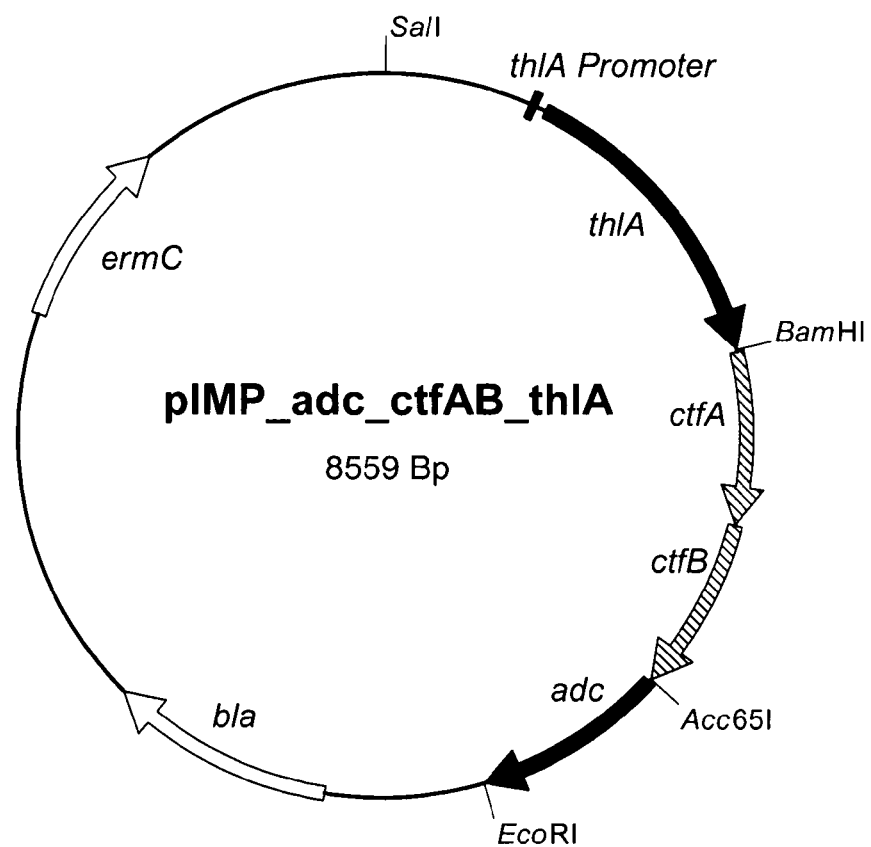

FIG. 3: Plasmid map pUC_adc_ctfAB_thlA:

FIG. 4: Plasmid map pIMP_adc_ctfAB_thlA:

EXAMPLES

Example 1

Cloning of the Expression Vectors

For acetone production in acetogenic cells, clonings into *E. coli* XL2 blue were carried out. For this, the genes ctfA and ctfB from *Clostridium acetobutylicum*,
or atoA and atoD from *E. coli*,
or teII from *B. subtilis*,
and/or ybgC from *Haemophilus influenzae*
together with the genes thlA and adc from *C. acetobutylicum* were arranged on the plasmid pIMP1 (Mermelstein et al., 1992).

An overview of the corresponding expression plasmids is presented in Table 1.

TABLE 1

| Plasmid | CoA-transferase/thioesterase from | Seq ID No |
|---|---|---|
| pIMP_adc_ctfAB_thlA | *C. acetobutylicum* | 13 |
| pIMP_adc_atoDA_thlA | *E. coli* | 14 |
| pIMP_adc_teII_thlA | *B. subtilis* | 15 |
| pIMP_adc_ybgC_thlA | *H. influenzae* | 16 |

The genes were cloned sequentially. For this, firstly oligonucleotides (Table 2) were designed for amplification of the genes, introducing corresponding cleavage sites, and then all fragments were amplified.

TABLE 1

Oligonucleotides

| Name | Sequence (5' → 3') * | Cleavage site | Seq ID No |
|---|---|---|---|
| adc fw | GGAAGGTACCTTTTATG | Acc65I | 1 |
| adc rev | GTAACTCTGAATTCTATTACTTAAG | EcoRI | 2 |
| atoDA fw | CACAACGGTGGATCCAAGAG | BamHI | 3 |
| atoDA rev | CGCGATATGGTACCAATCAT | Acc65I | 4 |
| ctfAB fw | GAATTTAAAAGGAGGGATCCAAATGAAC | BamHI | 5 |
| ctfAB rev | GTTTCATAGTATTGGTACCTAAACAGC | Acc65I | 6 |
| thl fw | CTCAGGTCGACTTCAAGAAG | SalI | 7 |
| thl rev | CAGAGTTATTTTTAAGGATCCTTTCTAGC | BamHI | 8 |
| teII fw | CAATTGGGATCCGATAACAATTTCACACAG | BamHI | 9 |
| teII rev | GAGATCTGGTACCCGGTTAAATGATCGGA | Acc65I | 10 |
| ybgc fw | CTCTAGAAGGATCCTGTTTAACTTTAAG | BamHI | 11 |
| ybgc rev | ATTGGGTACCTCATTGCATACTCCG | Acc65I | 12 |

Corresponding fragments were amplified by genomic DNA using conventional PCR techniques, separated electrophoretically and purified.

Generation of pUC_adc_ctfAB_thlA:

In the first step, adc was cloned via the cleavage sites Acc65I and EcoRI into the vector pUC18 and then thlA was added via SalI and BamHI. In the last step, ctfA and ctfB were cloned in one step, as it is organized as operon in *C. acetobutylicum*, via the cleavage sites BamHI and Acc65I. In the resultant vector pUC_adc_ctfAB_thlA, the genes required for acetone production are now organized in an operon.

FIG. 3 shows the resultant pUC plasmid.

Generation of pIMP_adc_ctfAB_thlA:

Next, the gene cassette is recloned into the vector pIMP1 via the restriction endonucleases SalI and EcoRI, resulting in the expression plasmid pIMP_adc_ctfAB_thlA, cf. FIG. 4.

Generation of pIMP_adc_atoDA_thlA, pIMP_adc_teII_thlA and pIMP_adc_ybgC_thlA:

For generating the vectors pIMP_adc_atoDA_thlA, pIMP_adc_teII_thlA and pIMP_adc_ybgC_thlA, the genes ctfA and ctfB were cut out of the vector pIMP_adc_ctfAB_thlA via the cleavage sites BamHI and Acc65I. atoD and atoA, which are organized in one operon in *E. coli*, were amplified, as well as the genes teII from *B. subtilis* and ybgC from *H. influenzae*, generating the cleavage sites BamHI and Acc65I.

These fragments were first cloned via this into the vector pDrive (atoDA) or pUC19 (teII and ybgC). Then these genes were recloned from the pDrive or pUC vectors, for which the gene cassettes were cut via the cleavage sites BamHI and Acc65I, purified and ligated into the vector backbone of pIMP_adc_ctfAB_thlA that had been restricted as described above (Acc65I and BamHI) and purified.

Example 2

Acetone Synthesis in *E. coli*

To check for functionality, all plasmid variants obtained (see Table 1) were investigated for acetone formation in the *E. coli* cloning strain XL2-blue. The analyses were performed at the 100-ml scale in TY medium with ampicillin (100 μg/ml). After inoculation from corresponding precultures to an optical density (600 nm) of 0.1, incubation was carried out at 37° C. and 150 rpm. The optical density was monitored photometrically and at specified timepoints, over a period of approx. 50 h, samples were taken and the concentration of acetone and acetate in the cell-free supernatant was determined by gas chromatography. It was found that with the combination of clostridial genes (thlA and adc) with atoDA from *E. coli*, up to 80 mM acetone was produced. With purely clostridial genes (thlA, ctfAB, adc), 5 mM acetone was produced, and with the combinations of clostridial genes (thlA and adc) with teII from *B. subtilis* or ybgC from *H. influenzae*, 1 mM acetone was produced.

Example 3

Acetogenic Acetone Production

Different media were used, depending on the Clostridia strain employed:

For preparation of the media for *C. carboxidivorans* or *C. ljungdahlii*, the chemicals were weighed, dissolved in water and then the pH was adjusted. In addition, the redox indicator reszurin (1 mg/l) was added, to permit later testing of the redox potential and therefore of the oxygen content. Then the media were brought to the boil in a heating mantle and cooled in an ice bath. During this, gassing was carried out with nitrogen, to remove the dissolved oxygen. Then the media were transferred into the anaerobic chamber, the final volume was adjusted with anaerobic water, it was filled and sealed hermetically. If a gas phase other than nitrogen was to be used, gas exchange was carried out, wherein the medium was gassed with the corresponding gas by means of a long cannula and finally a slight excess pressure of approx. 0.8 bar was applied.

For the medium for *C. aceticum*, all components were weighed, dissolved and filled. In addition the redox indicator reszurin (1 mg/l) was added, to allow subsequent testing for the redox potential and therefore the oxygen content. Then gassing was carried out via cannulas with a mixture of 80% $N_2$ and 20% $CO_2$, until a pH of 7.4 was reached. Once again, a slight excess pressure was applied. After autoclaving, sterile $Na_2CO_3$ was added in the form of an anaerobic 5% $Na_2CO_3$ solution added, to obtain a pH of 8.2. Additionally, fructose was added in sterile conditions to a final concentration of 1%. For autotrophic growth, a gas atmosphere of 80% $H_2$ and 20% $CO_2$ was produced. All media were autoclaved for 15 min at 121° C. and 1.2 bar. Some constituents of the media were autoclaved separately, to prevent chemical reactions of the components with one another. Heat-labile components were dissolved, sterile-filtered and were added to the cooled, autoclaved medium before use.

For the production of solid media, 1.5% (w/v) agar was added before autoclaving and directly thereafter they were poured into Petri dishes in the anaerobic chamber. After pouring, the plates were dried for a few days and were stored at 4° C. until use.

| Medium for *C. aceticum* | | |
|---|---|---|
| $NH_4Cl$ | 1.00 g | 18.7 mM |
| $KH_2PO_4$ | 0.33 g | 2.4 mM |
| $K_2HPO_4$ | 0.45 g | 2.6 mM |
| $MgSO_4 \times 7 H_2O$ | 0.10 g | 0.4 mM |
| Trace-element solution (s.u.) | 20.00 ml | 2% (v/v) |
| Wolfe's vitamin solution (s.u.) | 20.00 ml | 2% (v/v) |
| Yeast extract | 2.00 g | 0.2% (w/v) |
| $NaHCO_3$ | 10.00 g | 0.1M |
| Cysteine-HCl × $H_2O$ | 0.50 g | 2.8 mM |
| $Na_2S \times 9 H_2O$ | 0.50 g | 2.1 mM |
| Water | to 1000 ml | |

After autoclaving, 25 ml l–1 of a 5 wt. % $Na_2CO_3$ solution was added in sterile conditions, to obtain a pH of 8.2. Additionally, fructose was added in sterile conditions to a final concentration of 1 wt. % relative to the total medium. For autotrophic growth, a gas atmosphere of 80 vol. % $H_2$ and 20 vol. % $CO_2$ was produced before autoclaving.

| Medium for *C. carboxidivorans* - Wilkins-Chalgren Medium | | |
|---|---|---|
| Wilkins-Chalgren anaerobic broth (OXOID CM0643) | 33 g | 3.3% |
| $NaHCO_3$ | 1 g | 12 mM |
| Water | to 1000 ml | |

The pH was adjusted to 5.6 before boiling and anaerobization and after autoclaving, 10 ml of reducing agent 1 (see below) was added, after which the pH should be 6.0.

| Medium for *C. ljungdahlii* - ATCC Medium 1754 (PETC medium) | | |
|---|---|---|
| NH$_4$Cl | 1.0 g | 19 mM |
| KCl | 0.1 g | 1.35 mM |
| MgSO$_4$ * 7 H$_2$O | 0.2 g | 0.8 mM |
| NaCl | 0.8 g | 14 mM |
| KH$_2$PO$_4$ | 0.1 g | 0.7 mM |
| CaCl$_2$ * 2 H$_2$O | 20.0 mg | 0.15 mM |
| Yeast extract | 1.0 g | 0.1% (w/v) |
| Trace-element solution | 10.0 ml | 1% (v/v) |
| Wolfe's vitamin solution | 10.0 ml | 1% (v/v) |
| NaHCO$_3$ | 2.0 g | 24 mM |
| Water | to 1000 ml | pH 5.5 |

Before boiling and anaerobization, the pH was adjusted to 5.5. After autoclaving, 20 ml of a sterile fructose solution (250 g/l) and 5 ml each of reducing agent 1 and 2 (see below) were added, after which the pH should be 5.9.

Reducing Agent 1

1.8 g NaOH is dissolved in 200 ml water, boiled and cooled under nitrogen gassing. In the anaerobic chamber, first 4 g L-cysteine-HCl and then 4 g Na$_2$S*9H$_2$O are dissolved in 100 ml anaerobic NaOH and then autoclaved.

Reducing Agent 2

1.8 g NaOH is dissolved in 200 ml water, boiled and cooled under nitrogen gassing. In the anaerobic chamber, 4 g of L-cysteine-HCl is dissolved in 100 ml anaerobic NaOH and then autoclaved.

Trace-element solution for ATCC Medium 1754 and for the *C. aceticum* medium

| Nitrilotriacetic acid | 2 g | 10.5 mM |
|---|---|---|
| MnSO$_4$ * H$_2$O | 1 g | 6 mM |
| Fe(SO$_4$)$_2$ (NH4)$_2$ * 6 H$_2$O | 0.8 g | 2 mM |
| CoCl$_2$ * 6 H$_2$O | 0.2 g | 0.86 mM |
| ZnSO$_4$ * 7 H$_2$O | 0.2 mg | 0.7 µM |
| CuCl$_2$ * 2 H$_2$O | 20 mg | 0.12 mM |
| NiCl$_2$ * 6 H$_2$O | 20 mg | 80 µM |
| Na$_2$MoO$_4$ * 2 H$_2$O | 20 mg | 80 µM |
| Na2SeO4 | 20 mg | 80 µM |
| Na$_2$WO$_4$ | 20 mg | 60 µM |
| Water | to 1000 ml | |

First, the nitrilotriacetic acid was dissolved completely in water, the pH was adjusted to 6.0 with potassium hydroxide and then the other components were dissolved.

| Wolfe's vitamin solution for ATCC Medium 1754 and for the *C. aceticum* medium | | |
|---|---|---|
| Biotin (vitamin H) | 2.0 mg | 8 µM |
| Folic acid (vitamin B9) | 2.0 mg | 4.5 µM |
| Pyridoxine-HCl (vitamin B6) | 10.0 mg | 49 µM |
| Thiamin-HCl (vitamin B1) | 5.0 mg | 15 µM |
| Riboflavin (vitamin B2) | 5.0 mg | 13 µM |
| Nicotinamide (vitamin PP) | 5.0 mg | 41 µM |
| Calcium D-(+)-pantothenate | 5.0 mg | 10.5 µM |
| Cyanocobalmin (vitamin B12) | 0.1 mg | 74 µM |
| p-Aminobenzoic acid | 5.0 mg | 36 µM |
| Lipoic acid | 5.0 mg | 24 µM |
| Water | to 1000 ml | pH 4.3 |

The plasmids constructed in *E. coli* XL2-blue were then introduced into acetogenic Clostridia by conjugation (Purdy et al., 2002) or transformation (Zhu et al., 2004), so that the recombinant strain acquires the capacity to produce acetone.

For the conjugation experiments, the *E. coli* donor strain CA434 with the plasmid to be transferred was grown aerobically overnight in LB medium. A 1-ml aliquot was centrifuged for 1 min at 10000×g and the cell sediment was carefully suspended, in the anaerobic chamber, in 1 ml of sterile, anaerobic PBS buffer (1.5 mM KH$_2$PO$_4$, 4.2 mM Na$_2$HPO$_4$, 137 mM NaCl, 2.7 mM KCl), to prevent shearing-off of the conjugative pili. The cells were centrifuged again and were taken up in 200 µl of a *Clostridium* culture grown overnight in an appropriate medium. In the anaerobic chamber, this mixture was distributed on well-dried agar plates in 10-µl drops and incubated anaerobically at 37° C. for 6 h. Then the cells were washed from the agar plate 2-3 times with in each case 0.5 ml of sterile, anaerobic PBS buffer. The conjugation mixture was plated out on selective agar plates (clarithromycin) and incubated anaerobically at 37° C. For the transformation, the clostridial cells were grown in 50 ml of *C. aceticum* medium with 40 mM of DL-threonine at 30° C. to an optical density of 0.3-0.4. The next steps were carried out in the anaerobic chamber. Here, the cells were harvested (6000 rpm, 10 min, RT), washed twice with SMP buffer (270 mM sucrose, 1 mM MgCl$_2$, 7 mM NaH$_2$PO$_4$) and finally taken up in 500 to 700 µl SMP buffer and used in the transformation. For this, the cells were transferred to electroporation cuvettes (4 mm) and 0.5 to 1.5 µg plasmid-DNA was added. After incubation for 5 minutes, electroporation was carried out at 25 µF, 600Ω and 2.5 kV in a Gene-Pulser (Bio-Rad Laboratories GmbH; Munich) with 4 mM cuvettes (Biozym Scientific GmbH). Then the cells were added immediately to 5 ml of preheated medium. This was followed by incubation for resistance expression at 37° C. overnight for up to four days, and then 5 ml of medium was inoculated with clarithromycin (5 µg ml$^{-1}$) and incubated for 3 to 5 days at 37° C.

To verify the transformation, this was followed by plasmid isolation using a "peqGOLD® Plasmid Miniprep Kit II" (Pecilab, Erlangen). Preparation was carried out according to the manufacturer's instructions, carrying out all optional steps. Then plasmid recovery was carried out, using the *E. coli* strain XL2-blue, followed by restriction digestion.

All plasmid variants obtained (see Table 1) were investigated for acetone formation in the autotrophic Clostridia. The analyses were carried out at the 50-ml scale in the corresponding medium with clarithromycin (5 µg/ml). After inoculation from corresponding precultures, incubation was carried out at 37° C. The necessary gassing of the medium was carried out during preparation of the medium. Either synthesis gas or a CO$_2$/H$_2$ mixture in 1:2 ratio was used for this. The optical density was monitored photometrically and samples were taken at specified timepoints over a period of approx. 100 to 200 h and the concentration of acetone and acetate in the cell-free supernatant was determined by gas chromatography. It is found that with the combination clostridial genes (thlA and adc) with atoDA from *E. coli* and with the combinations clostridial genes (thlA and adc) with tell from *B. subtilis* or ybgC from *H. influenzae*, up to 1 mM acetone is produced. With purely clostridial genes (thlA, ctfAB, adc) up to 0.24 mM acetone was produced.

The invention claimed is:

1. An acetogenic cell that is able to form acetone and is genetically modified relative to its wild type, so that the acetogenic cell is able to form more acetone compared with its wild type,
wherein the acetogenic cell is able to utilize $CO_2$ as a terminal electron acceptor to form acetate, and
wherein the acetogenic cell is not *Clostridium acetobutylicum* or a genetically-modified variant thereof.

2. The acetogenic cell of claim 1, wherein the acetogenic cell is able to form acetone from at least one carbon source selected from the group consisting of carbon dioxide and carbon monoxide.

3. The acetogenic cell of claim 1, wherein the acetogenic cell, compared with its wild type, has an increased activity of at least one enzyme selected from the group consisting of:
(1) an enzyme which catalyzes the reaction of acetyl-coenzyme A to acetoacetyl-coenzyme A;
(2) an enzyme which catalyzes the reaction of acetoacetyl-coenzyme A to acetoacetate; and
(3) an enzyme which catalyzes the reaction of acetoacetate to acetone.

4. The acetogenic cell of claim 3, wherein
(1) is an acetyl-CoA-C-acetyl transferase (EC 2.3.1.9);
(2) is a butyrate-acetoacetate-CoA-transferase (EC 2.8.3.9) or an acyl-CoA-hydrolase (EC 3.1.2.20); and
(3) is an acetoacetate decarboxylase (EC 4.1.1.4).

5. The acetogenic cell of claim 1, wherein the acetogenic cell is a microorganism selected from the group consisting of *Thermoanaerobacter kivui, Acetobacterium woodii, Acetoanaerobium notera, Clostridium aceticum, Butyribacterium methylotrophicum, Moorella thermoacetica, Eubacterium limosum, Peptostreptococcus productus, Clostridium ljungdahlii* and *Clostridium carboxidivorans*.

6. The acetogenic cell of claim 2, wherein the acetogenic cell, compared with its wild type, has an increased activity of at least one enzyme selected from the group consisting of:
(1) an enzyme which catalyzes the reaction of acetyl-coenzyme A to acetoacetyl-coenzyme A;
(2) an enzyme which catalyzes the reaction of acetoacetyl-coenzyme A to acetoacetate; and
(3) an enzyme which catalyzes the reaction of acetoacetate to acetone.

7. The acetogenic cell of claim 5, wherein the acetogenic cell, compared with its wild type, has an increased activity of at least one enzyme selected from the group consisting of:
(1) an enzyme which catalyzes the reaction of acetyl-coenzyme A to acetoacetyl-coenzyme A;
(2) an enzyme which catalyzes the reaction of acetoacetyl-coenzyme A to acetoacetate; and
(3) an enzyme which catalyzes the reaction of acetoacetate to acetone.

8. The acetogenic cell of claim 3, which has an increased activity of (1) and wherein (1) is an acetyl-CoA-acetyl transferase (EC 2.3.1.9).

9. The acetogenic cell of claim 3, which has an increased activity of (2) and wherein (2) is a butyrate-acetoacetate-CoA-transferase (EC 2.8.3.9).

10. The acetogenic cell of claim 3, which has an increased activity of (2) and wherein (2) is an acyl-CoA-hydrolase (EC 3.1.2.20).

11. The acetogenic cell of claim 3, which has an increased activity of (3) and wherein (3) is an acetoacetate decarboxylase (EC 4.1.1.4).

12. The acetogenic cell of claim 3, which has an increased activity of (1) and (2) and wherein (1) is an acetyl-CoA-acetyl transferase (EC 2.3.1.9) and (2) is a butyrate-acetoacetate-CoA-transferase (EC 2.8.3.9).

13. The acetogenic cell of claim 11, which has an increased activity of (2) and wherein (2) is a butyrate-acetoacetate-CoA-transferase (EC 2.8.3.9).

14. The acetogenic cell of claim 3, which has an increased activity of (1) and (2) and wherein (1) is an acetyl-CoA-acetyl transferase (EC 2.3.1.9) and (2) is an acyl-CoA-hydrolase (EC 3.1.2.20).

15. The acetogenic cell of claim 3, which has an increased activity of (2) and (3) and wherein (2) is an acyl-CoA-hydrolase (EC 3.1.2.20) and (3) is an acetoacetate decarboxylase (EC 4.1.1.4).

16. The acetogenic cell of claim 3, which is a microorganism selected from the group consisting of *Thermoanaerobacter kivui, Acetobacterium woodii, Acetoanaerobium notera, Clostridium aceticum, Butyribacterium methylotrophicum, Moorella thermoacetica, Eubacterium limosum, Peptostreptococcus productus, Clostridium ljungdahlii* and *Clostridium carboxidivorans*.

17. The acetogenic cell of claim 1, which has an increased activity of (1) an enzyme which catalyzes the reaction of acetyl-coenzyme A to acetoacetyl-coenzyme A.

18. The acetogenic cell of claim 1, which has an increased activity of (2) an enzyme which catalyzes the reaction of acetoacetyl-coenzyme A to acetoacetate.

19. The acetogenic cell of claim 1, which has an increased activity of (3) an enzyme which catalyzes the reaction of acetoacetate to acetone.

20. A method for producing acetone, the method comprising:
A) contacting a cell of claim 1 with a nutrient medium comprising at least one carbon source selected from the group consisting of carbon dioxide and carbon monoxide; and B) cultivating the cell under at least one condition that enables the cell to form acetone.

21. The method of claim 20, further comprising isolating the acetone.

* * * * *

SEQUENCE LISTING

<160> NUMBER OF SEQ ID NOS: 16

<210> SEQ ID NO 1
<211> LENGTH: 17

<212> TYPE: DNA
<213> ORGANISM: Artificial
<220> FEATURE:
<223> OTHER INFORMATION: Primer

<400> SEQUENCE: 1
ggaaggtacc ttttatg                                                    17

<210> SEQ ID NO 2
<211> LENGTH: 25
<212> TYPE: DNA
<213> ORGANISM: Artificial
<220> FEATURE:
<223> OTHER INFORMATION: Primer

<400> SEQUENCE: 2
gtaactctga attctattac ttaag                                           25

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
cacaacggtg gatccaagag                                                 20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
cgcgatatgg taccaatcat                                                 20

<210> SEQ ID NO 5
<211> LENGTH: 28
<212> TYPE: DNA
<213> ORGANISM: Artificial
<220> FEATURE:
<223> OTHER INFORMATION: Primer

<400> SEQUENCE: 5
gaatttaaaa ggagggatcc aaatgaac                                        28

<210> SEQ ID NO 6
<211> LENGTH: 27
<212> TYPE: DNA
<213> ORGANISM: Artificial
<220> FEATURE:
<223> OTHER INFORMATION: Primer

<400> SEQUENCE: 6
gtttcatagt attggtacct aaacagc                                         27

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7

```
ctcaggtcga cttcaagaag                                                      20

<210> SEQ ID NO 8
<211> LENGTH: 29
<212> TYPE: DNA
<213> ORGANISM: Artificial
<220> FEATURE:
<223> OTHER INFORMATION: Primer

<400> SEQUENCE: 8
cagagttatt tttaaggatc ctttctagc                                            29

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
caattgggat ccgataacaa tttcacacag                                           30

<210> SEQ ID NO 10
<211> LENGTH: 29
<212> TYPE: DNA
<213> ORGANISM: Artificial
<220> FEATURE:
<223> OTHER INFORMATION: Primer

<400> SEQUENCE: 10
gagatctggt acccggttaa atgatcgga                                            29

<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11
ctctagaagg atcctgttta actttaag                                             28

<210> SEQ ID NO 12
<211> LENGTH: 25
<212> TYPE: DNA
<213> ORGANISM: Artificial
<220> FEATURE:
<223> OTHER INFORMATION: Primer

<400> SEQUENCE: 12
attgggtacc tcattgcata ctccg                                                25

<210> SEQ ID NO 13
<211> LENGTH: 8559
<212> TYPE: DNA
<213> ORGANISM: Artificial
<220> FEATURE:
<223> OTHER INFORMATION: Plasmid

<400> SEQUENCE: 13
agcttggctg caggtcgact tcaagaagag gcacctcatc ttggaaagcc tgtacttgtt          60
ttaagagatg ttactgaaag accagaagca gttgaggcag gaacggtaaa attagtagga        120
actgatatta aaaagatagt agacgaagcc tataaaataa tgaaagatga agaagaatat        180
gaaaaaatga gtaaggcaat aaatccatat ggtgatggaa aggcttcaga tagaatagtt        240
```

```
gatgctatat tgtatcattt tggagtatta aaggatagac cagatgaatt ttcacctaaa      300
aagtaataca tgagcattct aaaagaattt agaatgaagt ttcttatgca caagtatttt      360
ttattacatt aatatagtta aaatataaac ttatgtattt atgctaaaac atgattttaa      420
gggggttagc atatgcataa gtttaatttt tttgttaaaa aatattaaac tttgtgtttt      480
ttttaacaaa atatattgat aaaaataata atagtgggta taattaagtt gttagagaaa      540
acgtataaat tagggataaa ctatggaact tatgaaatag attgaaatgg tttatctgtt      600
accccgtatc aaaatttagg aggttagtta gaatgaaaga agttgtaata gctagtgcag      660
taagaacagc gattggatct tatggaaagt ctcttaagga tgtaccagca gtagatttag      720
gagctacagc tataaaggaa gcagttaaaa aagcaggaat aaaaccagag gatgttaatg      780
aagtcatttt aggaaatgtt cttcaagcag gtttaggaca gaatccagca agacaggcat      840
cttttaaagc aggattacca gttgaaattc cagctatgac tattaataag gtttgtggtt      900
caggacttag aacagttagc ttagcagcac aaattataaa agcaggagat gctgacgtaa      960
taatagcagg tggtatggaa atatgtctaa gagctcctta cttagcgaat aacgctagat     1020
ggggatatag aatgggaaac gctaaatttg ttgatgaaat gatcactgac ggattgtggg     1080
atgcatttaa tgattaccac atgggaataa cagcagaaaa catagctgag agatggaaca     1140
tttcaagaga agaacaagat gagtttgctc ttgcatcaca aaaaaaagct gaagaagcta     1200
taaaatcagg tcaatttaaa gatgaaatag ttcctgtagt aattaaaggc agaaagggag     1260
aaactgtagt tgatacagat gagcacccta gatttggatc aactatagaa ggacttgcaa     1320
aattaaaacc tgccttcaaa aaagatggaa cagttacagc tggtaatgca tcaggattaa     1380
atgactgtgc agcagtactt gtaatcatga gtgcagaaaa agctaaagag cttggagtaa     1440
aaccacttgc taagatagtt tcttatggtt cagcaggagt tgacccagca ataatgggat     1500
atggaccttt ctatgcaaca aaagcagcta ttgaaaaagc aggttggaca gttgatgaat     1560
tagatttaat agaatcaaat gaagcttttg cagctcaaag tttagcagta gcaaaagatt     1620
taaaatttga tatgaataaa gtaaatgtaa atggaggagc tattgcccct ggtcatccaa     1680
ttggagcatc aggtgcaaga atactcgtta ctccttgtaca cgcaatgcaa aaaagagatg     1740
caaaaaaagg cttagcaact ttatgtatag gtggcggaca aggaacagca atattgctag     1800
aaaagtgcta gaaaggatcc aaatgaactc taaaataatt agatttgaaa atttaaggtc     1860 attcttttaaa gatgggatga caattatgat tggaggtttt ttaaactgtg gcactccaac     1920
caaattaatt gattttttag ttaatttaaa tataaagaat ttaacgatta taagtaatga     1980
tacatgttat cctaatacag gtattggtaa gttaatatca aataatcaag taaaaaagct     2040
tattgcttca tatataggca gcaacccaga tactggcaaa aaactttta ataatgaact     2100 tgaagtagag ctctctcccc aaggaactct agtggaaaga atacgtgcag gcggatctgg     2160
cttaggtggt gtactaacta aaacaggttt aggaactttg attgaaaaag gaagaaaaa      2220 aatatctata aatggaacgg aatatttgtt agagctacct cttacagccg atgtagcatt     2280
aattaaaggt agtattgtag atgaggccgg aaacaccttc tataaaggta ctactaaaaa     2340
ctttaatccc tatatggcaa tggcagctaa accgtaata gttgaagctg aaaatttagt     2400
tagctgtgaa aaactagaaa aggaaaaagc aatgaccccc ggagttctta taaattatat     2460
agtaaaggag cctgcataaa atgattaatg ataaaaacct agcgaaagaa ataatagcca     2520
aaagagttgc aagagaatta aaaaatggtc aacttgtaaa cttaggtgta ggtcttccta     2580
```

-continued

```
ccatggttgc agattatata ccaaaaaatt tcaaaattac tttccaatca gaaaacggaa    2640
tagttggaat gggcgctagt cctaaaataa atgaggcaga taaagatgta gtaaatgcag    2700
gaggagacta tacaacagta cttcctgacg gcacattttt cgatagctca gtttcgtttt    2760
cactaatccg tggtggtcac gtagatgtta ctgttttagg ggctctccag gtagatgaaa    2820
agggtaatat agccaattgg attgttcctg gaaaaatgct ctctggtatg ggtggagcta    2880
tggatttagt aaatggagct aagaaagtaa taattgcaat gagacataca aataaaggtc    2940
aacctaaaat tttaaaaaaa tgtacacttc ccctcacggc aaagtctcaa gcaaatctaa    3000
ttgtaacaga acttggagta attgaggtta ttaatgatgg tttacttctc actgaaatta    3060
ataaaaacac aaccattgat gaaataaggt ctttaactgc tgcagattta ctcatatcca    3120
atgaacttag acccatggct gtttaggtac cttttatgtt aaaggatgaa gtaattaaac    3180
aaattagcac gccattaact tcgcctgcat ttcctagagg accctataaa tttcataatc    3240
gtgagtattt taacattgta tatcgtacag atatggatgc acttcgtaaa gttgtgccag    3300
agcctttaga aattgatgag cccttagtca ggtttgaaat tatggcaatg catgatacga    3360
gtggacttgg ttgttataca gaaagcggac aggctattcc cgtaagcttt aatggagtta    3420
agggagatta tcttcatatg atgtatttag ataatgagcc tgcaattgca gtaggaaggg    3480
aattaagtgc atatcctaaa aagctcgggt atccaaagct ttttgtggat tcagatactt    3540
tagtaggaac tttagactat ggaaaactta gagttgcgac agctacaatg gggtacaaac    3600
ataaagcctt agatgctaat gaagcaaagg atcaaatttg tcgccctaat tatatgttga    3660
aaataatacc caattatgat ggaagcccta gaatatgtga gcttataaat gcgaaaatca    3720
cagatgttac cgtacatgaa gcttggacag gaccaactcg actgcagtta tttgatcacg    3780
ctatggcgcc acttaatgat ttgccagtaa aagagattgt ttctagctct cacattcttg    3840
cagatataat attgcctaga gctgaagtta tatatgatta tcttaagtaa tagaattcac    3900
tggccgtcgt tttacaacgt cgtgactggg aaaaccctgg cgttacccaa cttaatcgcc    3960
ttgcagcaca tccccctttc gccagctggc gtaatagcga agaggcccgc accgatcgcc    4020
cttcccaaca gttgcgcagc ctgaatgcg aatggcgcct gatgcggtat tttctcctta    4080
cgcatctgtg cggtatttca caccgcatat ggtgcactct cagtacaatc tgctctgatg    4140
ccgcatagtt aagccagccc cgacacccgc caacacccgc tgacgcgccc tgacgggctt    4200
gtctgctccc ggcatccgct tacagacaag ctgtgaccgt ctccgggagc tgcatgtgtc    4260
agaggttttc accgtcatca ccgaaacgcg cgagacgaaa gggcctcgtg atacgcctat    4320
ttttataggt taatgtcatg ataataatgg tttcttagac gtcaggtggc acttttcggg    4380
gaaatgtgcg cggaacccct atttgtttat ttttctaaat acattcaaat atgtatccgc    4440
tcatgagaca ataaccctga taaatgcttc aataatattg aaaaaggaag agtatgagta    4500
ttcaacattt ccgtgtcgcc cttattccct tttttgcggc attttgcctt cctgtttttg    4560
ctcacccaga aacgctggtg aaagtaaaag atgctgaaga tcagttgggt gcacgagtgg    4620
gttacatcga actggatctc aacagcggta agatccttga gttttcgc cccgaagaac    4680
gttttccaat gatgagcact tttaaagttc tgctatgtgg cgcggtatta tcccgtattg    4740
acgccgggca agagcaactc ggtcgccgca tacactattc tcagaatgac ttggttgagt    4800
actcaccagt cacagaaaag catcttacgg atggcatgac agtaagagaa ttatgcagtg    4860
ctgccataac catgagtgat aacactgcgg ccaacttact tctgacaacg atcggaggac    4920
cgaaggagct aaccgctttt ttgcacaaca tgggggatca tgtaactcgc cttgatcgtt    4980
```

```
gggaaccgga gctgaatgaa gccataccaa acgacgagcg tgacaccacg atgcctgtag    5040
caatggcaac aacgttgcgc aaactattaa ctggcgaact acttactcta gcttcccggc    5100
aacaattaat agactggatg gaggcggata aagttgcagg accacttctg cgctcggccc    5160
ttccggctgg ctggtttatt gctgataaat ctggagccgg tgagcgtggg tctcgcggta    5220
tcattgcagc actggggcca gatggtaagc cctcccgtat cgtagttatc tacacgacgg    5280
ggagtcaggc aactatggat gaacgaaata gacagatcgc tgagataggt gcctcactga    5340
ttaagcattg gtaactgtca gaccaagttt actcatatat actttagatt gatttaaaac    5400
ttcattttta atttaaaagg atctaggtga agatccttt tgataatctc atgaccaaaa     5460
tcccttaacg tgagttttcg ttccactgag cgtcagaccc cgtagaaaag atcaaaggat    5520
cttcttgaga tccttttttt ctgcgcgtaa tctgctgctt gcaaacaaaa aaaccaccgc    5580
taccagcggt ggtttgtttg ccggatcaag agctaccaac tcttttccg aaggtaactg     5640 gcttcagcag agcgcagata ccaaatactg tccttctagt gtagccgtag ttaggccacc    5700
acttcaagaa ctctgtagca ccgcctacat acctcgctct gctaatcctg ttaccagtgg    5760
ctgctgccag tggcgataag tcgtgtctta ccgggttgga ctcaagacga tagttaccgg    5820
ataaggcgca gcggtcgggc tgaacggggg gttcgtgcac acagcccagc ttggagcgaa    5880
cgacctacac cgaactgaga tacctacagc gtgagctatg agaaagcgcc acgcttcccg    5940
aagggagaaa ggcggacagg tatccggtaa gcggcagggt cggaacagga gagcgcacga    6000
gggagcttcc agggggaaac gcctggtatc tttatagtcc tgtcgggttt cgccacctct    6060
gacttgagcg tcgatttttg tgatgctcgt caggggggcg gagcctatgg aaaaacgcca    6120
gcaacgcggc ctttttacgg ttcctggcct tttgctggcc ttttgctcac atgttctttc     6180
ctgcgttatc ccctgattct gtggataacc gtattaccgc ctttgagtga gctgataccg    6240
ctcgccgcag ccgaacgacc gagcgcagcg agtcagtgag cgaggaagcg gaagagcgcc    6300
caatacgcaa accgcctctc cccgcgcgtt ggccgattca ttaatgcagc tggcacgaca    6360
ggtttcccga ctggaaagcg ggcagtgagc gcaacgcaat taatgtgagt tagctcactc    6420
attaggcacc ccaggcttta cactttatgc ttccggctcg tatgttgtgt ggaattgtga    6480
gcggataaca atttcacaca ggaaacagct atgaccatga ttacgccaag ctttggctaa    6540
cacacacgcc attccaacca atagttttct cggcataaag ccatgctctg acgcttaaat    6600
gcactaatgc cttaaaaaaa cattaaagtc taacacacta gacttattta cttcgtaatt    6660
aagtcgttaa accgtgtgct ctacgaccaa agtataaaa cctttaagaa cttcttttt      6720 tcttgtaaaa aaagaaacta gataaatctc tcatatcttt tattcaataa tcgcatcaga    6780
ttgcagtata aatttaacga tcactcatca tgttcatatt tatcagagct cgtgctataa    6840
ttatactaat tttataagga ggaaaaaata aagagggtta taatgaacga gaaaaatata    6900
aaacacagtc aaaactttat tacttcaaaa cataatatag ataaaataat gacaaatata    6960
agattaaatg aacatgataa tatctttgaa atcggctcag gaaaagggca ttttacccctt    7020 gaattagtac agaggtgtaa tttcgtaact gccattgaaa tagaccataa attatgcaaa    7080
actacagaaa ataaacttgt tgatcacgat aatttccaag ttttaaacaa ggatatattg    7140
cagtttaaat ttcctaaaaa ccaatcctat aaaatatttg gtaatatacc ttataacata    7200
agtacggata taatacgcaa aattgttttt gatagtatag ctgatgagat ttatttaatc    7260
gtggaatacg ggtttgctaa aagattatta aatacaaaac gctcattggc attattttta    7320
```

| | |
|---|---|
| atggcagaag ttgatatttc tatattaagt atggttccaa gagaatattt tcatcctaaa | 7380 |
| cctaaagtga atagctcact tatcagatta aatagaaaaa aatcaagaat atcacacaaa | 7440 |
| gataaacaga agtataatta tttcgttatg aaatgggtta acaaagaata caagaaaata | 7500 |
| tttacaaaaa atcaatttaa caattcctta aaacatgcag gaattgacga tttaaacaat | 7560 |
| attagctttg aacaattctt atctcttttc aatagctata aattatttaa taagtaagtt | 7620 |
| aagggatgca taaactgcat cccttaactt gttttcgtg tacctatttt ttgtgaatcg | 7680 |
| attatgtctt ttgcgcattc acttcttttc tatataaata tgagcgaagc gaataagcgt | 7740 |
| cggaaaagca gcaaaaagtt tccttttgc tgttggagca tgggggttca gggggtgcag | 7800 |
| tatctgacgt caatgccgag cgaaagcgag ccgaagggta gcatttacgt tagataaccc | 7860 |
| cctgatatgc tccgacgctt tatatagaaa agaagattca actaggtaaa atcttaatat | 7920 |
| aggttgagat gataaggttt ataaggaatt tgtttgttct aatttttcac tcattttgtt | 7980 |
| ctaatttctt ttaacaaatg ttcttttttt tttagaacag ttatgatata gttagaatag | 8040 |
| tttaaaataa ggagtgagaa aaagatgaaa gaaagatatg gaacagtcta taaaggctct | 8100 |
| cagaggctca tagacgaaga aagtggagaa gtcatagagg tagacaagtt ataccgtaaa | 8160 |
| caaacgtctg gtaacttcgt aaaggcatat atagtgcaat taataagtat gttagatatg | 8220 |
| attggcggaa aaaacttaa aatcgttaac tatatcctag ataatgtcca cttaagtaac | 8280 |
| aatacaatga tagctacaac aagagaaata gcaaagcta caggaacaag tctacaaaca | 8340 |
| gtaataacaa cacttaaaat cttagaagaa ggaaatatta taaaaagaaa aactggagta | 8400 |
| ttaatgttaa accctgaact actaatgaga ggcgacgacc aaaaacaaaa atacctctta | 8460 |
| ctcgaatttg ggaactttga gcaagaggca aatgaaatag attgacctcc caataacacc | 8520 |
| acgtagttat tgggaggtca atctatgaaa atgcgatta | 8559 |

<210> SEQ ID NO 14
<211> LENGTH: 8563
<212> TYPE: DNA
<213> ORGANISM: Artificial
<220> FEATURE:
<223> OTHER INFORMATION: Plasmid

<400> SEQUENCE: 14

| | |
|---|---|
| agcttggctg caggtcgact tcaagaagag gcacctcatc ttggaaagcc tgtacttgtt | 60 |
| ttaagagatg ttactgaaag accagaagca gttgaggcag gaacggtaaa attagtagga | 120 |
| actgatatta aaaagatagt agacgaagcc tataaaataa tgaaagatga agaagaatat | 180 |
| gaaaaaatga gtaaggcaat aaatccatat ggtgatggaa aggcttcaga tagaatagtt | 240 |
| gatgctatat tgtatcattt tggagtatta aaggatagac cagatgaatt ttcacctaaa | 300 |
| aagtaataca tgagcattct aaaagaattt agaatgaagt ttcttatgca caagtatttt | 360 |
| ttattacatt aatatagtta aaatataaac ttatgtattt atgctaaaac atgattttaa | 420 |
| gggggttagc atatgcataa gtttaatttt tttgttaaaa aatattaaac tttgtgtttt | 480 |
| ttttaacaaa atatattgat aaaaataata atagtgggta taattaagtt gttagagaaa | 540 |
| acgtataaat tagggataaa ctatggaact tatgaaatag attgaaatgg tttatctgtt | 600 |
| accccgtatc aaaatttagg aggttagtta gaatgaaaga agttgtaata gctagtgcag | 660 |
| taagaacagc gattggatct tatgaaaagt ctcttaagga tgtaccagca gtagatttag | 720 |
| gagctacagc tataaaggaa gcagttaaaa aagcaggaat aaaaccagag gatgttaatg | 780 |
| aagtcatttt aggaaatgtt cttcaagcag gtttaggaca gaatccagca agacaggcat | 840 |

```
cttttaaagc aggattacca gttgaaattc cagctatgac tattaataag gtttgtggtt    900
caggacttag aacagttagc ttagcagcac aaattataaa agcaggagat gctgacgtaa    960
taatagcagg tggtatggaa aatatgtcta gagctcctta cttagcgaat aacgctagat   1020
ggggatatag aatgggaaac gctaaatttg ttgatgaaat gatcactgac ggattgtggg   1080
atgcatttaa tgattaccac atgggaataa cagcagaaaa catagctgag agatggaaca   1140
tttcaagaga agaacaagat gagtttgctc ttgcatcaca aaaaaagct gaagaagcta    1200
taaaatcagg tcaatttaaa gatgaaatag ttcctgtagt aattaaaggc agaaagggag   1260
aaactgtagt tgatacagat gagcaccta gatttggatc aactatagaa ggacttgcaa    1320
aattaaaacc tgccttcaaa aaagatggaa cagttacagc tggtaatgca tcaggattaa   1380
atgactgtgc agcagtactt gtaatcatga gtgcagaaaa agctaaagag cttgagtaa    1440
aaccacttgc taagatagtt tcttatggtt cagcaggagt tgacccagca ataatgggat   1500
atggaccttt ctatgcaaca aaagcagcta ttgaaaaagc aggttggaca gttgatgaat   1560
tagatttaat agaatcaaat gaagcttttg cagctcaaag tttagcagta gcaaaagatt   1620
taaaatttga tatgaataaa gtaaatgtaa atggaggagc tattgccctt ggtcatccaa   1680
ttggagcatc aggtgcaaga atactcgtta ctcttgtaca cgcaatgcaa aaaagagatg   1740
caaaaaagg cttagcaact ttatgtatag gtggcggaca aggaacagca atattgctag   1800
aaaagtgcta gaaaggatcc aagagggata aaaaatgaaa acaaaattga tgacattaca   1860
agacgccacc ggcttctttc gtgacggcat gaccatcatg gtgggcggat ttatggggat   1920
tggcactcca tcccgcctgg ttgaagcatt actggaatct ggtgttcgcg acctgacatt   1980
gatagccaat gataccgcgt tgttgatac cggcatcggt ccgctcatcg tcaatggtcg    2040
agtccgcaaa gtgattgctt cacatatcgg caccaacccg gaaacaggtc ggcgcatgat   2100
atctggtgag atggacgtcg ttctggtgcc gcaaggtacg ctaatcgagc aaattcgctg   2160
tggtggagct ggacttggtg ttttctcac cccaacgggt gtcggcaccg tcgtagagga    2220
aggcaaacag acactgacac tcgacggtaa aacctggctg ctcgaacgcc cactgcgcgc   2280
cgacctggcg ctaattcgcg ctcatcgttg cgacacactt ggcaacctga cctatcaact   2340
tagcgcccgc aactttaacc ccctgatagc ccttgcggct gatatcacgc tggtagagcc   2400
agatgaactg gtcgaaaccg gcgagctgca acctgaccat attgtcaccc ctggtgccgt   2460
tatcgaccac atcatcgttt cacaggagag caaataatgg atgcgaaaca acgtattgcg   2520
cgccgtgtgg cgcaagagct tcgtgatggt gacatcgtta acttagggat cggtttaccc   2580
acaatggtcg ccaattattt accggagggt attcatatca ctctgcaatc ggaaaacggc   2640
ttcctcggtt taggcccggt cacgacagcg catccagatc tggtgaacgc tggcgggcaa   2700
ccgtgcggtg ttttacccgg tgcagccatg tttgatagcg ccatgtcatt tgcgctaatc   2760
cgtggcggtc atattgatgc ctgcgtgctc ggcggttttgc aagtagacga agaagcaaac   2820
ctcgcgaact gggtagtgcc tgggaaaatg gtgcccggta tgggtggcgc gatggatctg   2880
gtgaccgggt cgcgcaaagt gatcatcgcc atggaacatt gcgccaaaga tggttcagca   2940
aaaatttgc gccgctgcac catgccactc actgcgcaac atgcggtgca tatgctggtt   3000
actgaactgg ctgtctttcg ttttattgac ggcaaaatgt ggctcaccga aattgccgac   3060
gggtgtgatt tagccaccgt gcgtgccaaa acagaagctc ggtttgaagt cgccgccgat   3120
ctgaatacgc aacggggtga tttatgattg gtaccttta tgttaaagga tgaagtaatt   3180
```

```
aaacaaatta gcacgccatt aacttcgcct gcatttccta gaggacccta taaatttcat    3240
aatcgtgagt attttaacat tgtatatcgt acagatatgg atgcacttcg taaagttgtg    3300
ccagagcctt tagaaattga tgagcccctta gtcaggtttg aaattatggc aatgcatgat   3360
```

```
aaacaaatta gcacgccatt aacttcgcct gcatttccta gaggacccta taaatttcat    3240
aatcgtgagt attttaacat tgtatatcgt acagatatgg atgcacttcg taaagttgtg    3300
ccagagcctt tagaaattga tgagccctta gtcaggtttg aaattatggc aatgcatgat    3360
acgagtggac ttggttgtta tacagaaagc ggacaggcta ttcccgtaag ctttaatgga    3420
gttaagggag attatcttca tatgatgtat ttagataatg agcctgcaat tgcagtagga    3480
agggaattaa gtgcatatcc taaaaagctc gggtatccaa agcttttttgt ggattcagat   3540
actttagtag gaactttaga ctatggaaaa cttagagttg cgacagctac aatggggtac    3600
aaacataaag ccttagatgc taatgaagca aaggatcaaa tttgtcgccc taattatatg    3660
ttgaaaataa tacccaatta tgatggaagc cctagaatat gtgagcttat aaatgcgaaa    3720
atcacagatg ttaccgtaca tgaagcttgg acaggaccaa ctcgactgca gttatttgat    3780
cacgctatgg cgccacttaa tgatttgcca gtaaaagaga ttgtttctag ctctcacatt    3840
cttgcagata taatattgcc tagagctgaa gttatatatg attatcttaa gtaatagaat    3900
tcactggccg tcgttttaca acgtcgtgac tgggaaaacc ctggcgttac ccaacttaat    3960
cgccttgcag cacatccccc tttcgccagc tggcgtaata gcgaagaggc ccgcaccgat    4020
cgcccttccc aacagttgcg cagcctgaat ggcgaatggc gcctgatgcg gtattttctc    4080
cttacgcatc tgtgcggtat ttcacaccgc atatggtgca ctctcagtac aatctgctct    4140
gatgccgcat agttaagcca gccccgacac ccgccaacac ccgctgacgc gccctgacgg    4200
gcttgtctgc tcccggcatc cgcttacaga caagctgtga ccgtctccgg gagctgcatg    4260
tgtcagaggt tttcaccgtc atcaccgaaa cgcgcgagac gaaagggcct cgtgatacgc    4320
ctatttttat aggttaatgt catgataata atggtttctt agacgtcagg tggcacttttt   4380
cggggaaatg tgcgcggaac ccctatttgt ttatttttct aaatacattc aaatatgtat    4440
ccgctcatga caataaacc ctgataaatg cttcaataat attgaaaaag gaagagtatg     4500
agtattcaac atttccgtgt cgcccttatt ccctttttgc ggcattttgc cttcctgtt     4560
tttgctcacc cagaaacgct ggtgaaagta aaagatgctg aagatcagtt gggtgcacga    4620
gtgggttaca tcgaactgga tctcaacagc ggtaagatcc ttgagagttt tcgccccgaa    4680
gaacgttttc caatgatgag cacttttaaa gttctgctat gtggcgcggt attatcccgt    4740
attgacgccg ggcaagagca actcggtcgc cgcatacact attctcagaa tgacttggtt    4800
gagtactcac cagtcacaga aaagcatctt acggatggca tgacagtaag agaattatgc    4860
agtgctgcca taaccatgag tgataacact gcggccaact tacttctgac aacgatcgga    4920
ggaccgaagg agctaaccgc ttttttgcac aacatggggg atcatgtaac tcgccttgat    4980
cgttgggaac cggagctgaa tgaagccata ccaaacgacg agcgtgacac cacgatgcct    5040
gtagcaatgg caacaacgtt gcgcaaacta ttaactggcg aactacttac tctagcttcc    5100
cggcaacaat taatagactg gatggaggcg gataaagttg caggaccact tctgcgctcg    5160
gcccttccgg ctggctggtt tattgctgat aaatctggag ccggtgagcg tgggtctcgc    5220
ggtatcattg cagcactggg gccagatggt aagccctccc gtatcgtagt tatctacacg    5280
acggggagtc aggcaactat ggatgaacga atatagacaga tcgctgagat aggtgcctca    5340
ctgattaagc attggtaact gtcagaccaa gtttactcat atatacttta gattgattta    5400
aaacttcatt tttaatttaa aaggatctag gtgaagatcc ttttgataa tctcatgacc     5460
aaaatccctt aacgtgagtt ttcgttccac tgagcgtcag accccgtaga aaagatcaaa    5520
ggatcttctt gagatccttt ttttctgcgc gtaatctgct gcttgcaaac aaaaaaacca    5580
```

```
ccgctaccag cggtggtttg tttgccggat caagagctac caactctttt tccgaaggta    5640
actggcttca gcagagcgca gataccaaat actgtccttc tagtgtagcc gtagttaggc    5700
caccacttca agaactctgt agcaccgcct acatacctcg ctctgctaat cctgttacca    5760
gtggctgctg ccagtggcga taagtcgtgt cttaccgggt tggactcaag acgatagtta    5820
ccggataagg cgcagcggtc gggctgaacg ggggttcgt gcacacagcc cagcttggag     5880
cgaacgacct acaccgaact gagatacccta cagcgtgagc tatgagaaag cgccacgctt    5940
cccgaaggga gaaaggcgga caggtatccg gtaagcggca gggtcggaac aggagagcgc    6000
acgagggagc ttccaggggg aaacgcctgg tatctttata gtcctgtcgg gtttcgccac    6060
ctctgacttg agcgtcgatt tttgtgatgc tcgtcagggg ggcggagcct atggaaaaac    6120
gccagcaacg cggccttttt acggttcctg gccttttgct ggccttttgc tcacatgttc    6180
tttcctgcgt tatcccctga ttctgtggat aaccgtatta ccgcctttga gtgagctgat    6240
accgctcgcc gcagccgaac gaccgagcgc agcgagtcag tgagcgagga agcggaagag    6300
cgcccaatac gcaaaccgcc tctccccgcg cgttggccga ttcattaatg cagctggcac    6360
gacaggtttc ccgactggaa agcgggcagt gagcgcaacg caattaatgt gagttagctc    6420
actcattagg caccccaggc tttacacttt atgcttccgg ctcgtatgtt gtgtggaatt    6480
gtgagcggat aacaatttca cacaggaaac agctatgacc atgattacgc caagctttgg    6540
ctaacacaca cgccattcca accaatagtt ttctcggcat aaagccatgc tctgacgctt    6600
aaatgcacta atgcccttaaa aaacattaa agtctaacac actagactta tttacttcgt     6660
aattaagtcg ttaaaccgtg tgctctacga ccaaaagtat aaaacccttta agaactttct    6720 tttttcttgt aaaaaaagaa actagataaa tctctcatat ctttttattca ataatcgcat    6780 cagattgcag tataaattta acgatcactc atcatgttca tatttatcag agctcgtgct    6840
ataattatac taattttata aggaggaaaa aataaagagg gttataatga acgagaaaaa    6900
tataaaacac agtcaaaact ttattacttc aaaacataat atagataaaa taatgacaaa    6960
tataagatta aatgaacatg ataatatctt tgaaatcggc tcaggaaaag ggcattttac    7020
ccttgaatta gtacagaggt gtaatttcgt aactgccatt gaaatagacc ataaattatg    7080
caaaactaca gaaaataaac ttgttgatca cgataatttc caagttttaa acaaggatat    7140
attgcagttt aaatttccta aaaaccaatc ctataaaata tttggtaata taccttataa    7200
cataagtacg gatataatac gcaaaattgt ttttgatagt atagctgatg agatttattt    7260
aatcgtggaa tacgggtttg ctaaaagatt attaaataca aaacgctcat ggcattatt    7320 tttaatggca gaagttgata tttctatatt aagtatggtt ccaagagaat attttcatcc    7380
taaacctaaa gtgaatagct cacttatcag attaaataga aaaaaatcaa gaatatcaca    7440
caaagataaa cagaagtata attatttcgt tatgaaatgg gttaacaaag aatacaagaa    7500
aatatttaca aaaaatcaat ttaacaattc cttaaaacat gcaggaattg acgatttaaa    7560
caatattagc tttgaacaat tcttatctct tttcaatagc tataaattat ttaataagta    7620
agttaaggga tgcataaact gcatccctta acttgttttt cgtgtaccta tttttgtga    7680 atcgattatg tcttttgcgc attcacttct tttctatata aatatgagcg aagcgaataa    7740
gcgtcggaaa agcagcaaaa agtttccttt ttgctgttgg agcatggggg ttcaggggt    7800 gcagtatctg acgtcaatgc cgagcgaaag cgagccgaag ggtagcattt acgttagata    7860
accccctgat atgctccgac gctttatata gaaaagaaga ttcaactagg taaaatctta    7920
```

| | |
|---|---:|
| atataggttg agatgataag gtttataagg aatttgtttg ttctaatttt tcactcattt | 7980 |
| tgttctaatt tcttttaaca aatgttcttt tttttttaga acagttatga tatagttaga | 8040 |
| atagtttaaa ataaggagtg agaaaaagat gaaagaaaga tatggaacag tctataaagg | 8100 |
| ctctcagagg ctcatagacg aagaaagtgg agaagtcata gaggtagaca agttataccg | 8160 |
| taaacaaacg tctggtaact tcgtaaaggc atatatagtg caattaataa gtatgttaga | 8220 |
| tatgattggc ggaaaaaaac ttaaaatcgt taactatatc ctagataatg tccacttaag | 8280 |
| taacaataca atgatagcta caacaagaga aatagcaaaa gctacaggaa caagtctaca | 8340 |
| aacagtaata acaacactta aaatcttaga agaaggaaat attataaaaa gaaaaactgg | 8400 |
| agtattaatg ttaaaccctg aactactaat gagaggcgac gaccaaaaac aaaaatacct | 8460 |
| cttactcgaa tttgggaact ttgagcaaga ggcaaatgaa atagattgac ctcccaataa | 8520 |
| caccacgtag ttattgggag gtcaatctat gaaaatgcga tta | 8563 |

<210> SEQ ID NO 15
<211> LENGTH: 8004
<212> TYPE: DNA
<213> ORGANISM: Artificial
<220> FEATURE:
<223> OTHER INFORMATION: Plasmid

<400> SEQUENCE: 15

| | |
|---|---:|
| agcttggctg caggtcgact tcaagaagag gcacctcatc ttggaaagcc tgtacttgtt | 60 |
| ttaagagatg ttactgaaag accagaagca gttgaggcag gaacggtaaa attagtagga | 120 |
| actgatatta aaaagatagt agacgaagcc tataaaataa tgaaagatga agaagaatat | 180 |
| gaaaaaatga gtaaggcaat aaatccatat ggtgatggaa aggcttcaga tagaatagtt | 240 |
| gatgctatat tgtatcattt tggagtatta aaggatagac cagatgaatt ttcacctaaa | 300 |
| aagtaataca tgagcattct aaaagaattt agaatgaagt ttcttatgca caagtatttt | 360 |
| ttattacatt aatatagtta aaatataaac ttatgtattt atgctaaaac atgattttaa | 420 |
| gggggttagc atatgcataa gtttaatttt tttgttaaaa aatattaaac tttgtgtttt | 480 |
| ttttaacaaa atatattgat aaaaataata atagtgggta taattaagtt gttagagaaa | 540 |
| acgtataaat tagggataaa ctatggaact tatgaaatag attgaaatgg tttatctgtt | 600 |
| accccgtatc aaaatttagg aggttagtta gaatgaaaga agttgtaata gctagtgcag | 660 |
| taagaacagc gattggatct tatggaaagt ctcttaagga tgtaccagca gtagatttag | 720 |
| gagctacagc tataaaggaa gcagttaaaa aagcaggaat aaaaccagag gatgttaatg | 780 |
| aagtcatttt aggaaatgtt cttcaagcag gtttaggaca gaatccagca agacaggcat | 840 |
| cttttaaagc aggattacca gttgaaattc cagctatgac tattaataag gtttgtggtt | 900 |
| caggacttag aacagttagc ttagcagcac aaattataaa agcaggagat gctgacgtaa | 960 |
| taatagcagg tggtatggaa aatatgtcta gagctcctta cttagcgaat aacgctagat | 1020 |
| ggggatatag aatgggaaac gctaaatttg ttgatgaaat gatcactgac ggattgtggg | 1080 |
| atgcatttaa tgattaccac atgggaataa cagcagaaaa catagctgag agatggaaca | 1140 |
| tttcaagaga agaacaagat gagtttgctc ttgcatcaca aaaaaaagct gaagaagcta | 1200 |
| taaaatcagg tcaatttaaa gatgaaatag ttcctgtagt aattaaaggc agaaagggag | 1260 |
| aaactgtagt tgatacagat gagcacccta gatttggatc aactatagaa ggacttgcaa | 1320 |
| aattaaaacc tgccttcaaa aaagatggaa cagttacagc tggtaatgca tcaggattaa | 1380 |
| atgactgtgc agcagtactt gtaatcatga gtgcagaaaa agctaaagag cttggagtaa | 1440 |

```
aaccacttgc taagatagtt tcttatggtt cagcaggagt tgacccagca ataatgggat   1500
atggaccttt ctatgcaaca aaagcagcta ttgaaaaagc aggttggaca gttgatgaat   1560
tagatttaat agaatcaaat gaagcttttg cagctcaaag tttagcagta gcaaaagatt   1620
taaaatttga tatgaataaa gtaaatgtaa atggaggagc tattgccctt ggtcatccaa   1680
ttggagcatc aggtgcaaga atactcgtta ctcttgtaca cgcaatgcaa aaagagatg    1740 caaaaaaagg cttagcaact ttatgtatag gtggcggaca aggaacagca atattgctag   1800
aaaagtgcta gaaaggatcc gataacaatt tcacacagaa ttcattaaag aggagaaatt   1860
aaccatgggc caactcttca aatcatttga tgcgtcggaa aaaacaccgc tcatctgttt   1920
tccgtttgcc ggcggctatt cggcgtcgtt tcgccctctc catgcttttt tgcaggggga   1980
gtgcgagatg ctcgctgccg agccgccggg acacggcacg aatcaaacgt cagccattga   2040
ggatctcgaa gagctgacgg atttgtacaa gcaagaactg aaccttcgcc ctgatcggcc   2100
gtttgtgctg ttcggacaca gtatgggcgg aatgatcacc ttcaggctgg cgcaaaagct   2160
tgagcgtgaa ggcatctttc gcaggcggt tatcatttct gcaatccagc cgcctcatat   2220
tcagcggagg aaagtgtccc acctgcctga tgatcagttt ctcgatcata ttatccaatt   2280
aggcggaatg cccgcagagc ttgttgaaaa taaggaggtc atgtcctttt tcctgccttc   2340
tttccgatca gattaccggg ctcttgaaca atttgagctt tacgatctgg cccagatcca   2400
gtcgcctgtt catgtcttta cgggcttga tgataaaaaa tgcatacgag atgcggaagg   2460
gtggaagaag tgggcaaaag acatcacatt ccatcaattt gacggcgggc acatgttcct   2520
gctgtcacaa acgaagaag tcgcagaacg gattttgcg atcttgaatc agcatccgat    2580
catttaaccg ggtaccttt atgttaaagg atgaagtaat taaacaaatt agcacgccat    2640
taacttcgcc tgcatttcct agaggaccct ataaatttca taatcgtgag tatttttaaca  2700 ttgtatatcg tacagatatg gatgcacttc gtaaagttgt gccagagcct ttagaaattg   2760
atgagcccct agtcaggttt gaaattatgg caatgcatga tacgagtgga cttggttgtt   2820
atacagaaag cggacaggct attcccgtaa gctttaatgg agttaaggga gattatcttc   2880
atatgatgta tttagataat gagcctgcaa ttgcagtagg aagggaatta agtgcatatc   2940
ctaaaaagct cgggtatcca aagcttttt tggattcaga tactttagta ggaactttag    3000
actatggaaa acttagagtt gcgacagcta caatgggta caaacataaa gccttagatg    3060
ctaatgaagc aaaggatcaa atttgtcgcc ctaattatat gttgaaaata atacccaatt    3120 atgatgaag cctagaata tgtgagctta taaatgcgaa aatcacagat gttaccgtac     3180
atgaagcttg gacaggacca actcgactgc agttatttga tcacgctatg gcgccactta   3240
atgatttgcc agtaaaagag attgtttcta gctctcacat tcttgcagat ataatattgc   3300
ctagagctga agttatatat gattatctta gtaatagaa ttcactggcc gtcgttttac    3360
aacgtcgtga ctgggaaaac cctggcgtta cccaacttaa tcgccttgca gcacatcccc   3420
ctttcgccag ctggcgtaat agcgaagagg cccgcaccga tcgcccttcc caacagttgc   3480
gcagcctgaa tggcgaatgg cgcctgatgc ggtattttct ccttacgcat ctgtgcggta   3540
tttcacaccg catatggtgc actctcagta caatctgctc tgatgccgca tagttaagcc   3600
agccccgaca cccgccaaca cccgctgacg cgccctgacg ggcttgtctg ctcccggcat   3660
ccgcttacag acaagctgtg accgtctccg ggagctgcat gtgtcagagg ttttcaccgt   3720
catcaccgaa acgcgcgaga cgaaagggcc tcgtgatacg cctatttta taggttaatg    3780
```

```
tcatgataat aatggtttct tagacgtcag gtggcacttt tcggggaaat gtgcgcggaa    3840
cccctatttg tttatttttc taaatacatt caaatatgta tccgctcatg agacaataac    3900
cctgataaat gcttcaataa tattgaaaaa ggaagagtat gagtattcaa catttccgtg    3960
tcgcccttat tcccttttttt gcggcatttt gccttcctgt ttttgctcac ccagaaacgc    4020
tggtgaaagt aaaagatgct gaagatcagt tgggtgcacg agtgggttac atcgaactgg    4080
atctcaacag cggtaagatc cttgagagtt ttcgccccga agaacgtttt ccaatgatga    4140
gcacttttaa agttctgcta tgtggcgcgg tattatcccg tattgacgcc gggcaagagc    4200
aactcggtcg ccgcatacac tattctcaga atgacttggt tgagtactca ccagtcacag    4260
aaaagcatct tacggatggc atgacagtaa gagaattatg cagtgctgcc ataaccatga    4320
gtgataacac tgcggccaac ttacttctga caacgatcgg aggaccgaag gagctaaccg    4380
cttttttgca caacatgggg gatcatgtaa ctcgccttga tcgttgggaa ccggagctga    4440
atgaagccat accaaacgac gagcgtgaca ccacgatgcc tgtagcaatg gcaacaacgt    4500
tgcgcaaact attaactggc gaactactta ctctagcttc ccggcaacaa ttaatagact    4560
ggatggaggc ggataaagtt gcaggaccac ttctgcgctc ggcccttccg gctggctggt    4620
ttattgctga taaatctgga gccggtgagc gtgggtctcg cggtatcatt gcagcactgg    4680
ggccagatgg taagccctcc cgtatcgtag ttatctacac gacggggagt caggcaacta    4740
tggatgaacg aaatagacag atcgctgaga taggtgcctc actgattaag cattggtaac    4800
tgtcagacca agtttactca tatatacttt agattgattt aaaacttcat ttttaattta    4860
aaaggatcta ggtgaagatc ctttttgata atctcatgac caaaatccct taacgtgagt    4920
tttcgttcca ctgagcgtca gaccccgtag aaaagatcaa aggatcttct tgagatcctt    4980
tttttctgcg cgtaatctgc tgcttgcaaa caaaaaaacc accgctacca gcggtggttt    5040
gtttgccgga tcaagagcta ccaactcttt ttccgaaggt aactggcttc agcagagcgc    5100
agataccaaa tactgtcctt ctagtgtagc cgtagttagg ccaccacttc aagaactctg    5160
tagcaccgcc tacatacctc gctctgctaa tcctgttacc agtggctgct gccagtggcg    5220
ataagtcgtg tcttaccggg ttggactcaa gacgatagtt accggataag gcgcagcggt    5280
cgggctgaac ggggggttcg tgcacacagc ccagcttgga gcgaacgacc tacaccgaac    5340
tgagatacct acagcgtgag ctatgagaaa gcgccacgct tcccgaaggg agaaaggcgg    5400
acaggtatcc ggtaagcggc agggtcggaa caggagagcg cacgagggag cttccagggg    5460
gaaacgcctg gtatctttat agtcctgtcg ggtttcgcca cctctgactt gagcgtcgat    5520
ttttgtgatg ctcgtcaggg gggcggagcc tatggaaaaa cgccagcaac gcggcctttt    5580
tacggttcct ggccttttgc tggccttttg ctcacatgtt ctttcctgcg ttatcccctg    5640
attctgtgga taaccgtatt accgcctttg agtgagctga taccgctcgc cgcagccgaa    5700
cgaccgagcg cagcgagtca gtgagcgagg aagcggaaga gcgcccaata cgcaaaccgc    5760
ctctccccgc gcgttggccg attcattaat gcagctggca cgacaggttt cccgactgga    5820
aagcgggcag tgagcgcaac gcaattaatg tgagttagct cactcattag gcaccccagg    5880
ctttacactt tatgcttccg gctcgtatgt tgtgtggaat tgtgagcgga taacaatttc    5940
acacaggaaa cagctatgac catgattacg ccaagctttg ctaacacac acgccattcc    6000
aaccaatagt tttctcggca taagccatg ctctgacgct taaatgcact aatgccttaa    6060
aaaaacatta aagtctaaca cactagactt atttacttcg taattaagtc gttaaaccgt    6120
gtgctctacg accaaaagta taaaaccttt aagaactttc tttttttcttg taaaaaaaga    6180
```

```
aactagataa atctctcata tcttttattc aataatcgca tcagattgca gtataaattt    6240
aacgatcact catcatgttc atatttatca gagctcgtgc tataattata ctaattttat    6300
aaggaggaaa aaataaagag ggttataatg aacgagaaaa atataaaaca cagtcaaaac    6360
tttattactt caaaacataa tatagataaa ataatgacaa atataagatt aaatgaacat    6420
gataatatct ttgaaatcgg ctcaggaaaa gggcatttta cccttgaatt agtacagagg    6480
tgtaatttcg taactgccat tgaaatagac cataaaattt gcaaaactac agaaaataaa    6540
cttgttgatc acgataattt ccaagtttta acaaggata tattgcagtt taaatttcct    6600
aaaaaccaat cctataaaat atttggtaat ataccttata acataagtac ggatataata    6660
cgcaaaattg ttttgatag tatagctgat gagatttatt taatcgtgga atacgggttt     6720
gctaaaagat tattaaatac aaaacgctca ttggcattat ttttaatggc agaagttgat    6780
atttctatat taagtatggt tccaagagaa tattttcatc ctaaacctaa agtgaatagc    6840
tcacttatca gattaaatag aaaaaaatca agaatatcac acaaagataa acagaagtat    6900
aattatttcg ttatgaaatg ggttaacaaa gaatacaaga aaatatttac aaaaaatcaa    6960
tttaacaatt ccttaaaaca tgcaggaatt gacgatttaa acaatattag ctttgaacaa    7020
ttcttatctc ttttcaatag ctataaatta tttaataagt aagttaaggg atgcataaac    7080
tgcatccctt aacttgtttt tcgtgtacct atttttttgtg aatcgattat gtcttttgcg    7140
cattcacttc ttttctatat aaatatgagc gaagcgaata agcgtcggaa aagcagcaaa    7200
aagtttcctt tttgctgttg gagcatgggg gttcagggg tgcagtatct gacgtcaatg      7260
ccgagcgaaa gcgagccgaa gggtagcatt tacgttagat aaccccctga tatgctccga    7320
cgctttatat agaaaagaag attcaactag gtaaaatctt aatataggtt gagatgataa    7380
ggtttataag gaatttgttt gttctaattt ttcactcatt ttgttctaat ttcttttaac    7440
aaatgttctt ttttttttag aacagttatg atatagttag aatagtttaa aataaggagt    7500
gagaaaaaga tgaagaaag atatggaaca gtctataaag gctctcagag gctcatagac    7560
gaagaaagtg gagaagtcat agaggtagac aagttatacc gtaaacaaac gtctggtaac    7620
ttcgtaaagg catatatagt gcaattaata agtatgttag atatgattgg cggaaaaaaa    7680
cttaaaatcg ttaactatat cctagataat gtccacttaa gtaacaatac aatgatagct    7740
acaacaagag aaatagcaaa agctacagga acaagtctac aaacagtaat aacaacactt    7800
aaaatcttag aagaggaaa tattataaaa agaaaaactg gagtattaat gttaaacct     7860 gaactactaa tgagaggcga cgaccaaaaa caaaaatacc tcttactcga atttgggaac    7920
tttgagcaag aggcaaatga aatagattga cctcccaata acaccacgta gttattggga    7980
ggtcaatcta tgaaaatgcg atta                                          8004
```

<210> SEQ ID NO 16
<211> LENGTH: 7693
<212> TYPE: DNA
<213> ORGANISM: Artificial
<220> FEATURE:
<223> OTHER INFORMATION: Plasmid

<400> SEQUENCE: 16

```
agcttggctg caggtcgact tcaagaagag gcacctcatc ttggaaagcc tgtacttgtt      60
ttaagagatg ttactgaaag accagaagca gttgaggcag gaacggtaaa attagtagga    120
actgatatta aaagatagt agcgaagcc tataaaataa tgaaagatga agaagaatat     180
```

```
gaaaaaatga gtaaggcaat aaatccatat ggtgatggaa aggcttcaga tagaatagtt     240
gatgctatat tgtatcattt tggagtatta aaggatagac cagatgaatt ttcacctaaa     300
aagtaataca tgagcattct aaaagaattt agaatgaagt ttcttatgca caagtatttt     360
ttattacatt aatatagtta aaatataaac ttatgtattt atgctaaaac atgattttaa     420
gggggttagc atatgcataa gtttaatttt tttgttaaaa aatattaaac tttgtgtttt     480
ttttaacaaa atatattgat aaaaataata atagtgggta taattaagtt gttagagaaa     540
acgtataaat tagggataaa ctatggaact tatgaaatag attgaaatgg tttatctgtt     600
accccgtatc aaaatttagg aggttagtta gaatgaaaga agttgtaata gctagtgcag     660
taagaacagc gattggatct tatggaaagt ctcttaagga tgtaccagca gtagatttag     720
gagctacagc tataaaggaa gcagttaaaa aagcaggaat aaaaccagag gatgttaatg     780
aagtcatttt aggaaatgtt cttcaagcag gtttaggaca gaatccagca agacaggcat     840 ctttttaaagc aggattacca gttgaaattc cagctatgac tattaataag gtttgtggtt     900
caggacttag aacagttagc ttagcagcac aaattataaa agcaggagat gctgacgtaa     960
taatagcagg tggtatggaa aatatgtcta gagctcctta cttagcgaat aacgctagat    1020
ggggatatag aatgggaaac gctaaatttg ttgatgaaat gatcactgac ggattgtggg    1080
atgcatttaa tgattaccac atgggaataa cagcagaaaa catagctgag agatggaaca    1140
tttcaagaga agaacaagat gagtttgctc ttgcatcaca aaaaaagct gaagaagcta    1200 taaaatcagg tcaatttaaa gatgaaatag ttcctgtagt aattaaaggc agaaagggag    1260
aaactgtagt tgatacagat gagcacccta gatttggatc aactatagaa ggacttgcaa    1320
aattaaaacc tgccttcaaa aaagatggaa cagttacagc tggtaatgca tcaggattaa    1380
atgactgtgc agcagtactt gtaatcatga gtgcagaaaa agctaaagag cttggagtaa    1440
aaccacttgc taagatagtt tcttatggtt cagcaggagt tgacccagca ataatgggat    1500
atggaccttt ctatgcaaca aaagcagcta ttgaaaaagc aggttggaca gttgatgaat    1560
tagatttaat agaatcaaat gaagcttttg cagctcaaag tttagcagta gcaaaagatt    1620
taaaatttga tatgaataaa gtaaatgtaa atggaggagc tattgccctt ggtcatccaa    1680
ttggagcatc aggtgcaaga atactcgtta ctcttgtaca cgcaatgcaa aaaagagatg    1740
caaaaaaagg cttagcaact ttatgtatag gtggcggaca aggaacagca atattgctag    1800
aaaagtgcta gaaaggatcc tgtttaactt taagaaggag atatacatat gttggataat    1860
ggcttttctt ttcctgttcg tgtgtattat gaagatactg atgcaggtgg cgtagtgtat    1920
cacgctcgct atttgcattt ttttgaacga gcaagaacag aatatttgcg tacattaaat    1980
tttacgcaac aaaccttact agaggaacaa caactcgcat tgttgtcaa aacgctcgcc    2040 attgattatt gcgtggcagc aaaattggat gatttactta tggtggaaac agaggtttca    2100
gaagtaaaag gggctacaat ccttttttgaa cagagactga tgcgcaacac cctgatgtta    2160
tcaaaggcta ctgttaaggt agcctgtgtt gatctaggca agatgaaacc agtggcgttt    2220
cccaaagaag ttaaagcggc gtttcatcac ttaaaataat ttttcggagt atgcaatgag    2280 gtaccttta tgttaaagga tgaagtaatt aaacaaatta gcacgccatt aacttcgcct    2340
gcatttccta gaggacccta taaatttcat aatcgtgagt attttaacat tgtatatcgt    2400
acagatatgg atgcacttcg taaagttgtg ccagagcctt tagaaattga tgagcccttaa    2460 gtcaggtttg aaattatggc aatgcatgat acgagtggac ttggttgtta tacagaaagc    2520
ggacaggcta ttcccgtaag cttaatggaa gttaagggag attatcttca tatgatgtat    2580
```

```
ttagataatg agcctgcaat tgcagtagga agggaattaa gtgcatatcc taaaaagctc    2640
gggtatccaa agcttttgt ggattcagat actttagtag aactttaga ctatggaaaa      2700 cttagagttg cgacagctac aatggggtac aaacataaag ccttagatgc taatgaagca    2760
aaggatcaaa tttgtcgccc taattatatg ttgaaaataa tacccaatta tgatggaagc    2820
cctagaatat gtgagcttat aaatgcgaaa atcacagatg ttaccgtaca tgaagcttgg    2880
acaggaccaa ctcgactgca gttatttgat cacgctatgg cgccacttaa tgatttgcca    2940
gtaaaagaga ttgtttctag ctctcacatt cttgcagata taatattgcc tagagctgaa    3000
gttatatatg attatcttaa gtaatagaat tcactggccg tcgttttaca acgtcgtgac    3060
tgggaaaacc ctggcgttac ccaacttaat cgccttgcag cacatccccc tttcgccagc    3120
tggcgtaata gcgaagaggc ccgcaccgat cgcccttccc aacagttgcg cagcctgaat    3180
ggcgaatggc gcctgatgcg gtattttctc cttacgcatc tgtgcggtat tcacaccgc     3240 atatggtgca ctctcagtac aatctgctct gatgccgcat agttaagcca gccccgacac    3300
ccgccaacac ccgctgacgc gccctgacgg gcttgtctgc tcccggcatc cgcttacaga    3360
caagctgtga ccgtctccgg gagctgcatg tgtcagaggt tttcaccgtc atcaccgaaa    3420
cgcgcgagac gaaagggcct cgtgatacgc ctatttttat aggttaatgt catgataata    3480
atggtttctt agacgtcagg tggcactttt cggggaaatg tgcgcggaac ccctatttgt    3540
ttatttttct aaatacattc aaatatgtat ccgctcatga caataaacc ctgataaatg      3600 cttcaataat attgaaaaag gaagagtatg agtattcaac atttccgtgt cgcccttatt    3660 ccctttttg cggcattttg ccttcctgtt tttgctcacc cagaaacgct ggtgaaagta      3720
aaagatgctg aagatcagtt gggtgcacga gtgggttaca tcgaactgga tctcaacagc    3780
ggtaagatcc ttgagagttt tcgccccgaa gaacgttttc caatgatgag cacttttaaa    3840
gttctgctat gtggcgcggt attatcccgt attgacgccg ggcaagagca actcggtcgc    3900
cgcatacact attctcagaa tgacttggtt gagtactcac cagtcacaga aaagcatctt    3960
acggatggca tgacagtaag agaattatgc agtgctgcca taaccatgag tgataacact    4020
gcggccaact tacttctgac aacgatcgga ggaccgaagg agctaaccgc tttttttgcac   4080 aacatggggg atcatgtaac tcgccttgat cgttgggaac cggagctgaa tgaagccata    4140
ccaaacgacg agcgtgacac cacgatgcct gtagcaatgg caacaacgtt gcgcaaacta    4200
ttaactggcg aactacttac tctagcttcc cggcaacaat taatagactg gatggaggcg    4260
gataaagttg caggaccact tctgcgctcg gcccttccgg ctggctggtt tattgctgat    4320
aaatctggag ccggtgagcg tgggtctcgc ggtatcattg cagcactggg gccagatggt    4380
aagccctccc gtatcgtagt tatctacacg acggggagtc aggcaactat ggatgaacga    4440
aatagacaga tcgctgagat aggtgcctca ctgattaagc attggtaact gtcagaccaa    4500
gtttactcat atatacttta gattgattta aaacttcatt tttaatttaa aaggatctag    4560
gtgaagatcc tttttgataa tctcatgacc aaaatccctt aacgtgagtt ttcgttccac    4620
tgagcgtcag accccgtaga aaagatcaaa ggatcttctt gagatccttt ttttctgcgc    4680
gtaatctgct gcttgcaaac aaaaaaacca ccgctaccag cggtggtttg tttgccggat    4740
caagagctac caactctttt tccgaaggta actggcttca gcagagcgca gataccaaat    4800
actgtccttc tagtgtagcc gtagttaggc caccacttca agaactctgt agcaccgcct    4860
acatacctcg ctctgctaat cctgttacca gtggctgctg ccagtggcga taagtcgtgt    4920
```

```
cttaccgggt tggactcaag acgatagtta ccggataagg cgcagcggtc gggctgaacg    4980
gggggttcgt gcacacagcc cagcttggag cgaacgacct acaccgaact gagataccta    5040
cagcgtgagc tatgagaaag cgccacgctt cccgaaggga gaaggcgga caggtatccg     5100 gtaagcggca gggtcggaac aggagagcgc acgagggagc ttccagggggg aaacgcctgg   5160 tatctttata gtcctgtcgg gtttcgccac ctctgacttg agcgtcgatt tttgtgatgc    5220
tcgtcagggg ggcggagcct atggaaaaac gccagcaacg cggccttttt acggttcctg    5280
gccttttgct ggccttttgc tcacatgttc tttcctgcgt tatcccctga ttctgtggat    5340
aaccgtatta ccgcctttga gtgagctgat accgctcgcc gcagccgaac gaccgagcgc    5400
agcgagtcag tgagcgagga agcggaagag cgcccaatac gcaaaccgcc tctccccgcg    5460
cgttggccga ttcattaatg cagctggcac gacaggtttc ccgactggaa agcgggcagt    5520
gagcgcaacg caattaatgt gagttagctc actcattagg caccccaggc tttacacttt    5580
atgcttccgg ctcgtatgtt gtgtggaatt gtgagcggat aacaatttca cacaggaaac    5640
agctatgacc atgattacgc caagctttgg ctaacacaca cgccattcca accaatagtt    5700
ttctcggcat aaagccatgc tctgacgctt aaatgcacta atgccttaaa aaaacattaa    5760
agtctaacac actagactta tttacttcgt aattaagtcg ttaaaccgtg tgctctacga    5820
ccaaaagtat aaaacctttta agaactttct ttttttcttgt aaaaaaagaa actagataaa   5880
tctctcatat cttttattca ataatcgcat cagattgcag tataaattta acgatcactc    5940
atcatgttca tatttatcag agctcgtgct ataattatac taatttttata aggaggaaaa    6000 aataagagg gttataatga acgagaaaaa tataaaacac agtcaaaact ttattacttc     6060
aaaacataat atagataaaa taatgacaaa tataagatta aatgaacatg ataatatctt    6120
tgaaatcggc tcaggaaaag ggcatttttac ccttgaatta gtacagaggt gtaatttcgt   6180
aactgccatt gaaatagacc ataaattatg caaaactaca gaaaataaac ttgttgatca    6240
cgataaattc caagttttaa acaaggatat attgcagttt aaatttccta aaaaccaatc    6300
ctataaaata tttggtaata taccttataa cataagtacg gatataatac gcaaaattgt    6360
ttttgatagt atagctgatg agatttattt aatcgtggaa tacgggtttg ctaaaagatt    6420
attaaataca aaacgctcat tggcattatt tttaatggca gaagttgata tttctatatt    6480
aagtatggtt ccaagagaat attttcatcc taaacctaaa gtgaatagct cacttatcag    6540
attaaataga aaaaatcaa gaatatcaca caaagataaa cagaagtata attatttcgt     6600
tatgaaatgg gttaacaaag aatacaagaa aatatttaca aaaaatcaat ttaacaattc    6660
cttaaaacat gcaggaattg acgatttaaa caatattagc tttgaacaat tcttatctct    6720
tttcaatagc tataaaattat ttaataagta agttaaggga tgcataaact gcatccctta   6780
acttgttttt cgtgtaccta ttttttgtga atcgattatg tcttttgcgc attcacttct    6840
tttctatata aatatgagcg aagcgaataa gcgtcggaaa agcagcaaaa agtttccttt    6900
ttgctgttgg agcatggggg ttcagggggt gcagtatctg acgtcaatgc cgagcgaaag    6960
cgagccgaag ggtagcattt acgttagata acccccctgat atgctccgac gctttatata   7020
gaaaagaaga ttcaactagg taaaatctta atataggttg agatgataag gtttataagg    7080
aatttgtttg ttctaatttt tcactcattt tgttctaatt tcttttaaca aatgttcttt    7140 ttttttttaga acagttatga tatagttaga atagtttaaa ataaggagtg agaaaaagat   7200 gaaagaaga tatggaacag tctataaagg ctctcagagg ctcatagacg aagaaagtgg     7260
agaagtcata gaggtagaca agttataccg taaacaaacg tctggtaact tcgtaaaggc    7320
```

-continued

```
atatatagtg caattaataa gtatgttaga tatgattggc ggaaaaaaac ttaaaatcgt    7380
taactatatc ctagataatg tccacttaag taacaataca atgatagcta caacaagaga    7440
aatagcaaaa gctacaggaa caagtctaca aacagtaata acaacactta aaatcttaga    7500
agaaggaaat attataaaaa gaaaaactgg agtattaatg ttaaaccctg aactactaat    7560
gagaggcgac gaccaaaaac aaaaatacct cttactcgaa tttgggaact ttgagcaaga    7620
ggcaaatgaa atagattgac ctcccaataa caccacgtag ttattgggag gtcaatctat    7680
gaaaatgcga tta                                                      7693
```